US010010670B2

(12) United States Patent
Burke et al.

(10) Patent No.: US 10,010,670 B2
(45) Date of Patent: Jul. 3, 2018

(54) PATIENT PROGRAMMER FOR IMPLANTABLE DRUG DELIVERY DEVICE

(71) Applicant: Flowonix Medical Incorporated, Mt. Olive, NJ (US)

(72) Inventors: Paul Burke, Bellingham, MA (US); Steve Adler, Randolph, NJ (US)

(73) Assignee: Flowonix Medical Incorporated, Mt. Olive, NJ (US)

( * ) Notice: Subject to any disclaimer, the term of this patent is extended or adjusted under 35 U.S.C. 154(b) by 0 days.

(21) Appl. No.: 15/632,988

(22) Filed: Jun. 26, 2017

(65) Prior Publication Data

US 2018/0001018 A1 Jan. 4, 2018

Related U.S. Application Data

(63) Continuation of application No. 15/098,631, filed on Apr. 14, 2016, now Pat. No. 9,700,669.
(Continued)

(51) Int. Cl.
*G08C 19/22* (2006.01)
*A61M 5/142* (2006.01)
(Continued)

(52) U.S. Cl.
CPC ....... *A61M 5/14276* (2013.01); *A61B 5/0026* (2013.01); *A61B 5/0031* (2013.01); *G06F 19/3468* (2013.01); *A61M 2005/14208* (2013.01); *A61M 2205/04* (2013.01); *A61M 2205/3523* (2013.01); *A61M 2205/3553* (2013.01); *A61M 2205/3592* (2013.01); *A61M 2205/52* (2013.01)

(58) Field of Classification Search
CPC .................................. A61M 5/14276
USPC ...................................... 340/870.07
See application file for complete search history.

(56) References Cited

U.S. PATENT DOCUMENTS 5,049,141 A 9/1991 Olive
6,361,522 B1 * 3/2002 Scheiner .................. A61N 1/30
128/DIG. 12
(Continued)

OTHER PUBLICATIONS

Notification of Transmittal of the International Search Report and Written Opinion for International Application No. PCT/US2016/027803, dated Sep. 2, 2016.
(Continued)

*Primary Examiner* — Santiago Garcia
(74) *Attorney, Agent, or Firm* — The Marbury Law Group, PLLC

(57) ABSTRACT

Methods for programming an implantable drug delivery device using a mobile computing device that include establishing a connection with a telemetry unit configured for wireless communication with the implantable drug delivery device, displaying user-selectable drug delivery settings for the implantable drug delivery device, receiving at least one selection of a drug delivery setting, translating the received selection into a signal format readable by the telemetry unit, and sending the translated signal to the telemetry unit to program the implantable drug delivery device. Further embodiments include telemetry units for communication with an implantable drug delivery device, and patient programmers and a method for patient modification to a programmed drug delivery regimen.

19 Claims, 14 Drawing Sheets

Related U.S. Application Data

(60) Provisional application No. 62/148,431, filed on Apr. 16, 2015.

(51) Int. Cl.
*A61B 5/00* (2006.01)
*G06F 19/00* (2018.01)

(56) References Cited

U.S. PATENT DOCUMENTS

| | | | | |
|---|---|---|---|---|
| 7,270,633 B1* | 9/2007 | Goscha | ............... | A61B 5/0031 600/300 |
| 8,115,618 B2* | 2/2012 | Robertson | .......... | A61B 1/00016 340/539.12 |
| 8,273,058 B2 | 9/2012 | Burke et al. | | |
| 8,932,221 B2* | 1/2015 | Colliou | ............... | A61B 5/0031 600/302 |
| 8,956,288 B2* | 2/2015 | Hafezi | ................... | H01M 8/08 600/300 |
| 8,961,412 B2* | 2/2015 | Hafezi | .................. | A61B 5/073 128/902 |
| 9,042,996 B2* | 5/2015 | Van Baelen | ....... | A61N 1/36032 607/57 |
| 9,270,025 B2* | 2/2016 | Robertson | ............ | A61B 5/0031 |
| 2003/0088295 A1* | 5/2003 | Cox | .................. | A61N 1/37282 607/60 |
| 2005/0175665 A1* | 8/2005 | Hunter | .................. | A61K 45/06 424/423 |
| 2005/0277912 A1* | 12/2005 | John | ................ | A61M 25/0026 604/890.1 |
| 2006/0271112 A1* | 11/2006 | Martinson | ............ | A61B 5/0031 607/2 |
| 2007/0135855 A1* | 6/2007 | Foshee | ................ | A61B 5/0031 607/31 |
| 2007/0197957 A1* | 8/2007 | Hunter | ................... | A61L 31/10 604/65 |
| 2007/0282634 A1* | 12/2007 | Johnson | ................ | G16H 50/70 705/3 |
| 2007/0299317 A1* | 12/2007 | Hoyme | .............. | G06F 19/3418 600/300 |
| 2008/0307435 A1* | 12/2008 | Rehman | .................. | G06F 9/542 719/318 |
| 2009/0082645 A1* | 3/2009 | Hafezi | .................. | A61B 5/073 600/302 |
| 2009/0093797 A1 | 4/2009 | Burke et al. | | |
| 2009/0105784 A1* | 4/2009 | Massoud-Ansari | ............... | A61N 1/36082 607/45 |
| 2010/0152534 A1* | 6/2010 | Kim | ....................... | A61B 1/041 600/109 |
| 2010/0152713 A1 | 6/2010 | Adler et al. | | |
| 2010/0156651 A1* | 6/2010 | Broer | ....................... | G01S 13/74 340/670 |
| 2010/0185055 A1* | 7/2010 | Robertson | ............ | A61B 5/0031 600/117 |
| 2010/0286592 A1 | 11/2010 | Girouard et al. | | |
| 2011/0037614 A1* | 2/2011 | Verhoef | .............. | G06F 19/3406 340/870.07 |
| 2011/0156907 A1* | 6/2011 | Nagai | ..................... | G06K 7/0008 340/572.1 |
| 2012/0232616 A1* | 9/2012 | Van Baelen | ........ | A61N 1/36032 607/57 |
| 2012/0265266 A1* | 10/2012 | Colborn | ............ | A61N 1/36053 607/45 |
| 2012/0277819 A1* | 11/2012 | Cowley | ................. | A61N 1/0556 607/45 |
| 2013/0147622 A1 | 6/2013 | LaLonde et al. | | |
| 2013/0172774 A1* | 7/2013 | Crowder | ................... | A61B 5/04 600/544 |
| 2014/0055284 A1* | 2/2014 | Tran | ..................... | A61B 5/0024 340/870.07 |
| 2014/0085104 A1* | 3/2014 | Rao | ...................... | A61B 5/0031 340/870.07 |
| 2014/0142549 A1* | 5/2014 | Su | ...................... | A61M 5/14276 604/512 |
| 2016/0183799 A1* | 6/2016 | San Vicente | ......... | A61B 5/0015 340/870.07 |

OTHER PUBLICATIONS

International Preliminary Report on Patentability for International Application No. PCT/US2016/027803, dated Oct. 26, 2017.

* cited by examiner

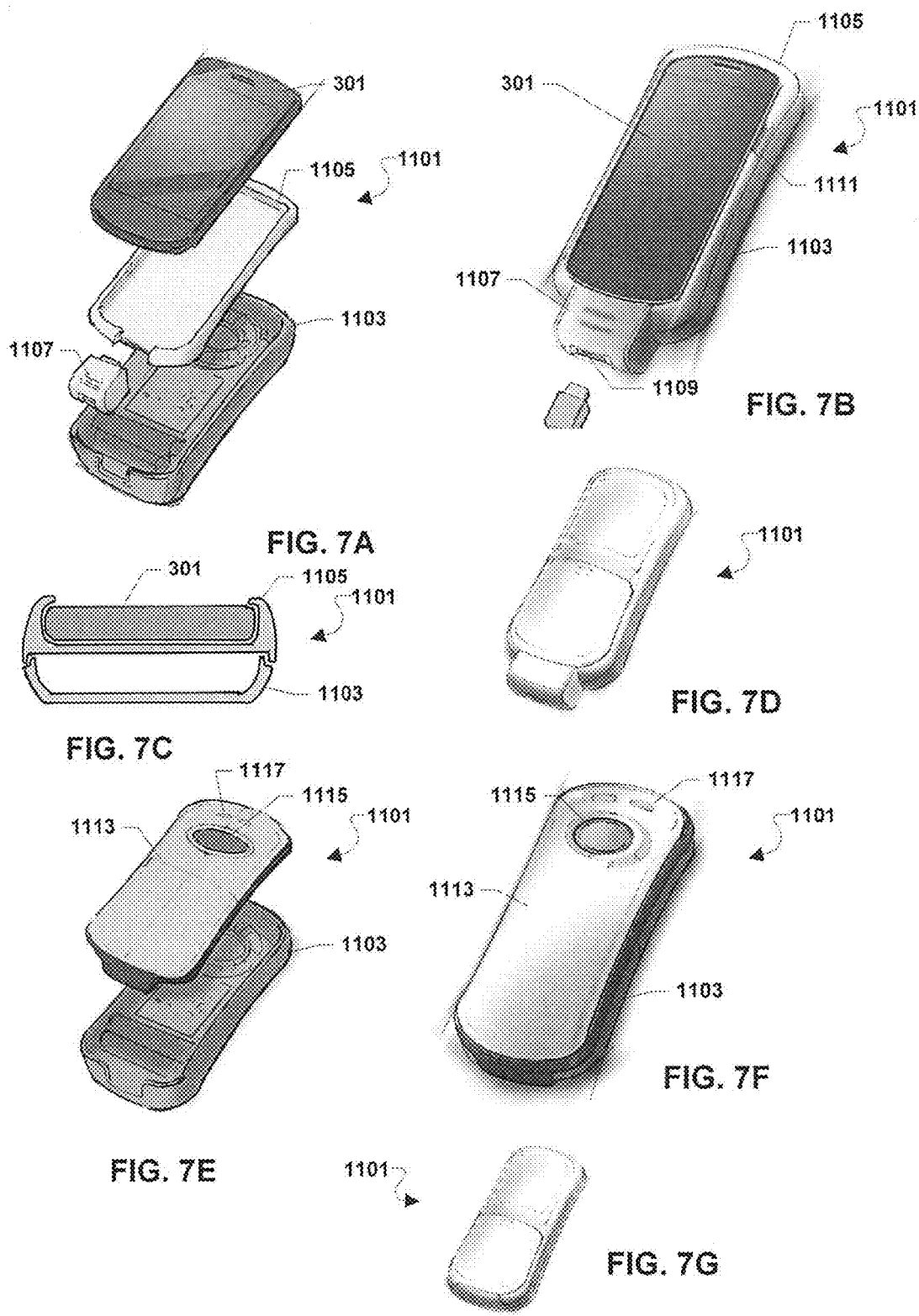

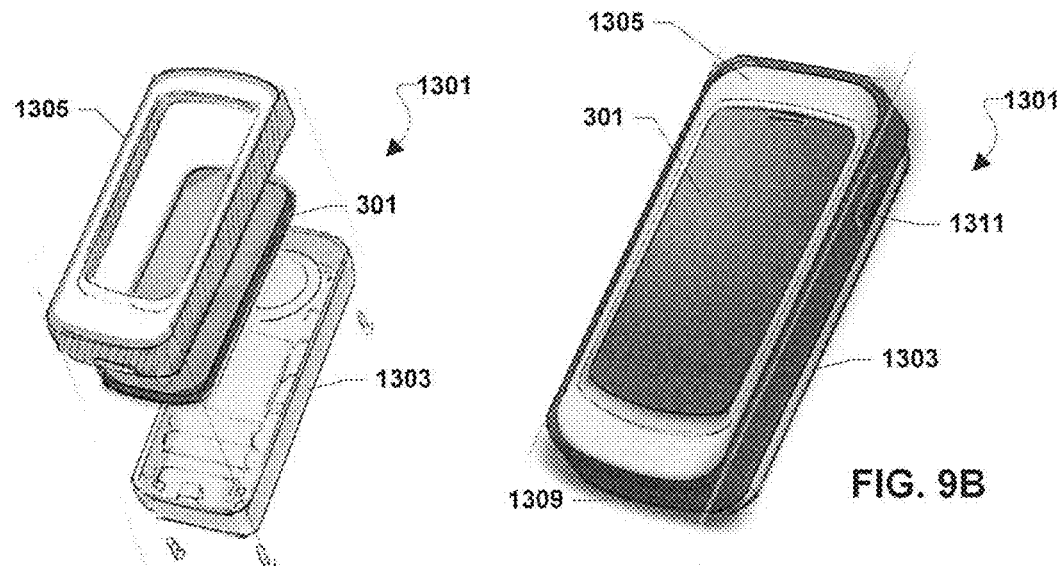
FIG. 9A
FIG. 9B
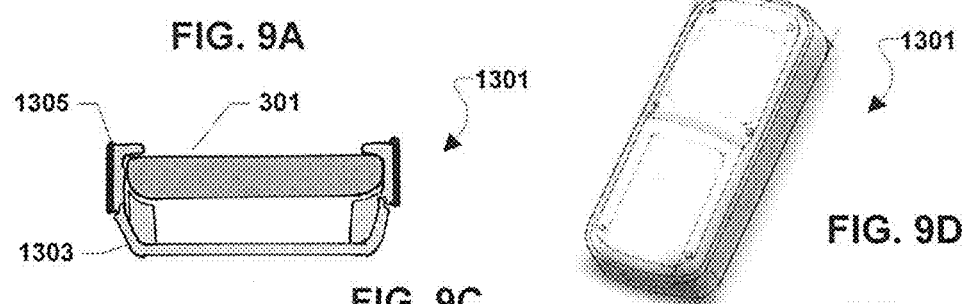
FIG. 9C
FIG. 9D
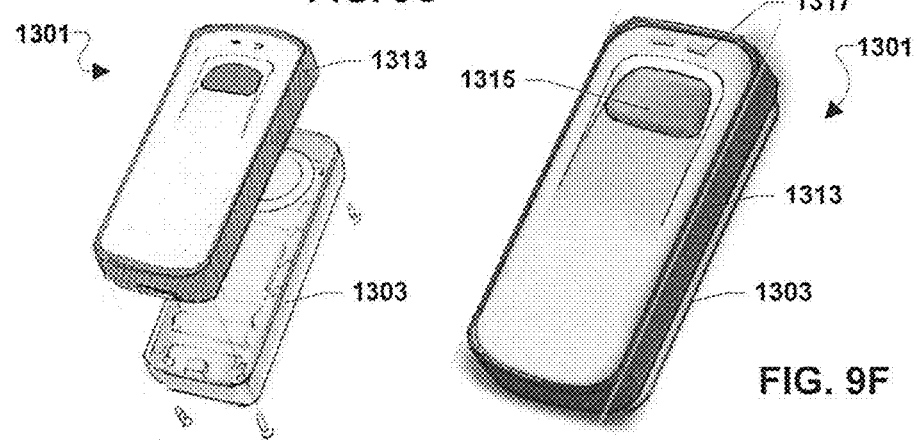
FIG. 9E
FIG. 9F
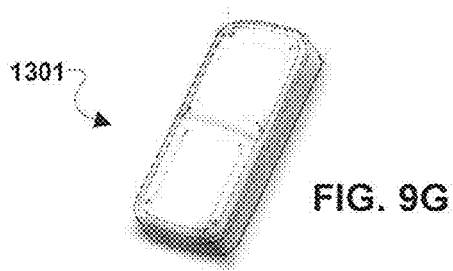
FIG. 9G

PATIENT PROGRAMMER FOR IMPLANTABLE DRUG DELIVERY DEVICE

RELATED APPLICATION

This application is a continuation of U.S. patent application Ser. No. 15/098,631 entitled "Patient Programmer for Implantable Drug Delivery Device" filed Apr. 14, 2016, which claimed the benefit of priority to U.S. Provisional Application No. 62/148,431, titled "Patient Programmer for Implantable Drug Delivery Device," filed Apr. 16, 2015, the entire contents of both of which are incorporated herein by reference.

FIELD

The present invention relates generally to systems and methods for programming an implantable drug delivery device.

BACKGROUND

Various implantable devices exist for delivering infusate, such as medication, to a patient. One such device is an implantable valve accumulator pump system. This system includes an electronically controlled metering assembly located between a drug reservoir and an outlet catheter. The metering assembly may include two normally closed solenoid valves that are positioned on the inlet and outlet sides of a fixed volume accumulator. The inlet valve opens to admit a fixed volume of infusate from the reservoir into the accumulator. Then, the inlet valve is closed and the outlet valve is opened to dispense the fixed volume of infusate from the accumulator to an outlet catheter through which the infusate is delivered to the patient. The valves may be controlled electronically via an electronics module, which can optionally be programmed utilizing an external programmer to provide a programmable drug delivery rate. The external programmer is typically a dedicated device used by medical professionals having a customized telemetry system for wirelessly communicating with the implantable drug delivery device.

SUMMARY

Various embodiments include programming and controlling the operation of implantable drug delivery devices using a commonly-used mobile computing device, such as mobile phones, tablet computers, and PDA's. Various embodiments also include telemetry units that may be physically coupled to a mobile computing device for programming of an implantable drug delivery device by a physician or other medical professional, and may also be used with a patient programmer to allow patient-initiated modifications to a programmed drug delivery regimen within parameters set by the physician. The various embodiments leverage the flexibility, user-intuitiveness, processing power and networking capabilities of commonly-used mobile computing devices for programming and control of an implantable drug delivery system, while simplifying the requirements of dedicated electronic devices associated with such systems.

Embodiments include a method for communicating with an implantable drug delivery device using a mobile computing device that includes establishing a connection with a telemetry unit configured for wireless communication with the implantable drug delivery device, displaying user-selectable drug delivery settings for the implantable drug delivery device, receiving at least one selection of a drug delivery setting, translating the received selection into a signal format readable by the telemetry unit, and sending the translated signal to the telemetry unit to program the implantable drug delivery device. In some embodiments, the method may further include receiving data from the implantable drug delivery device via the connection with the telemetry unit, such as data regarding a status of the implantable drug delivery device, physiological data of a patient in which the drug delivery device is implanted, or data regarding the programming of the implantable drug delivery device.

Further embodiments include a patient programmer and a method for patient modification to a programmed drug delivery regimen in an implantable drug delivery device that includes establishing a connection with a computing device, receiving from the computing device at least one parameter for patient modification of the programmed drug delivery regimen, storing the at least one parameter in a memory, detecting an input event corresponding to a patient request for modification to the programmed drug delivery regimen, determining whether the requested modification is allowed based on the stored at least one parameter, and transmitting the patient request to the implantable drug delivery device when it is determined that the requested modification is allowed.

Further embodiments include a telemetry unit for communication with an implantable drug delivery device that includes a transmitter/receiver element configured for wireless communication with the implantable drug delivery device, a communication module for establishing a communication link with a mobile communication device, and a housing containing the transmitter/receiver element and the communication module, the housing configured to secure the mobile communication device to the housing to physically couple the mobile communication device to the telemetry unit while the communication link with the mobile communication device is established.

Further embodiments include a telemetry unit for communication with an implantable drug delivery device that includes a transmitter/receiver element configured for wireless communication with the implantable drug delivery device, a communication module for establishing a communication link with a patient programmer unit having a user-input component configured to receive patient requests for modification to a drug delivery regimen programmed in the implantable drug delivery device, and a housing containing the transmitter/receiver element and the communication module, the housing configured to the secure patient programmer unit to the housing to physically couple the mobile communication device to the telemetry unit while the communication link with the patient programmer unit is established.

Various embodiments include mobile computing devices and patient programmers configured to perform operations of the embodiment methods disclosed herein. Various embodiments also include mobile computing devices and patient programmers including means for performing functions of the embodiment methods disclosed herein. Various embodiments also include non-transitory processor-readable storage media having stored thereon processor-executable instructions configured to cause a processor to perform operations of the embodiment methods disclosed herein.

BRIEF DESCRIPTION OF THE DRAWINGS

The accompanying drawings, which are incorporated herein and constitute part of this specification, illustrate example embodiments of the invention, and together with the general description given above and the detailed description given below, serve to explain the features of the invention.

FIGS. 7A-7G illustrate a telemetry unit usable for programming of a implantable drug delivery device and for patient modifications to a programmed drug delivery regimen according to one embodiment.

FIGS. 9A-9G illustrate a telemetry unit according to yet another embodiment.

FIGS. 10A-10G illustrate a telemetry unit according to yet another embodiment.

DETAILED DESCRIPTION

Figure 1A:
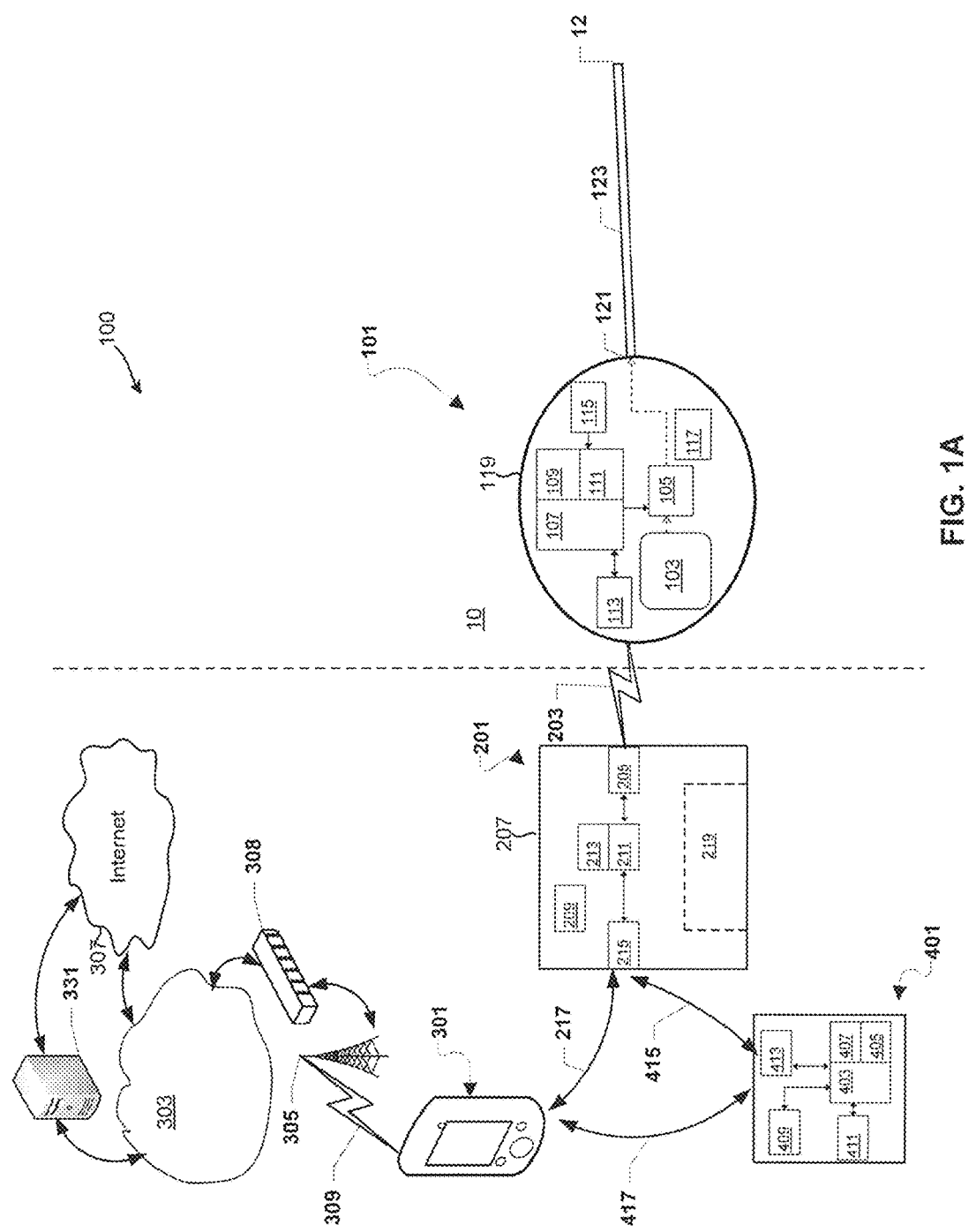
FIG. 1A is a schematic diagram of a system for programming and controlling an implantable drug delivery device using a mobile computing device, a telemetry unit and a patient programmer unit.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The word "exemplary" is used herein to mean "serving as an example, instance, or illustration." Any implementation described herein as "exemplary" is not necessarily to be construed as preferred or advantageous over other implementations.

The terms "mobile computing device," "mobile device," and "mobile communication device" are used interchangeably herein to refer to any one or all of tablet computers, smartphones, cellular telephones, personal digital assistants (PDA's), smartbooks, laptop computers, palm-top computers, and similar personal electronic devices which include a programmable processor and memory and may include hardware and/or software to enable communication with a telemetry unit for programming of an implantable drug delivery device.

Various embodiments include methods and systems for communicating with an implantable drug delivery device using a mobile computing device. The mobile computing device may include software, such as application software, configured to execute on a processor of the mobile computing device to enable the device to establish a connection with a telemetry unit configured for wireless communication with an implantable drug delivery device, display on a display of the mobile communication device user-selectable drug delivery settings for the implantable drug delivery device, receive from a user interface of the mobile communication device at least one selection of a drug delivery setting, translate the received selection into a signal format that can be read by the telemetry unit, and transmit the translated signals to the telemetry unit for programming of the mobile computing device. A mobile computing device executing the programming software may be used by medical personnel to program an implantable device with an initial drug delivery regimen, either before or after the device is implanted in the patient, and may also be used to re-program an implanted device with a new or modified drug delivery regimen. In various embodiments, the software process executing on the mobile device may be configured to receive data from the implantable drug delivery device, via the telemetry unit, such as current status data or historical data of the device (e.g., amount of drug dispensed and remaining to be dispensed, dosage history, etc.), as well as physiological data of the patient. In some embodiments, the software process executing on the mobile device may be used for inquiring an operational status (e.g., pump status) of the implantable drug delivery device as a means to remotely determine the current operation of the implantable drug delivery device.

Various embodiments may also enable programming of a patient programmer using a mobile computing device. A patient programmer may be a device, separate from the mobile computing device and usable by the patient to selectively modify a programmed drug delivery regimen within parameters set by the programming clinician. The mobile computing device may include software, such as application software, configured to execute on a processor of the mobile computing device to enable the device to establish a connection with a patient programmer device, display on a display of the mobile computing device user-selectable settings for the patient programmer device, receive from a user interface of the mobile computing device at least one selection of parameter for patient modification of a programmed drug delivery regimen, and transmit the at least one parameter to the patient programmer device to program the patient programmer device. Once programmed, the patient programmer device may be operable to selectively modify the programmed drug delivery regime, such as by administering a bolus dose of the drug, within the parameters programmed by the mobile computing device.

Various embodiments are directed to a patient programmer device for enabling a patient to selectively modify the drug delivery regimen of an implantable drug delivery device within parameters set by medical personnel. In embodiments, the patient programmer device may be a simple, easy-to-use device with limited functionality, such as functionality to enable a patient to administer an extra dose (i.e., a bolus dose) of the drug when needed. The patient programmer may include, at minimum, a user input component (e.g., a button) and circuitry configured to detect a patient input event from the user input component (e.g., a button push) and to communicate an instruction to modify the drug delivery regimen (e.g., by administering a bolus dose) to a telemetry unit configured for wireless communication with the implantable drug delivery device. The patient programmer device may further include communication circuitry configured to receive parameters related to allowable modifications to a programmed drug delivery regimen, a memory for storing the received parameters, and a processor, coupled to the memory for determining whether or not a proposed modification to the drug delivery regimen corresponding to a detected patient input event (e.g., a button push) is allowed based on the stored parameters. The patient programmer may also include a user feedback component, such as a display (e.g., an LCD screen, LED indicator(s), a touchscreen display, etc.) that may indicate whether or not a proposed user modification to the drug delivery regimen (e.g., a button push to request a bolus dose) was allowed and/or successfully implemented. In embodiments, a display of a patient programmer may also display information regarding the implantable drug delivery device and/or the programmed drug delivery regimen, such as current status data or historical data of the device (e.g., amount of drug dispensed and remaining to be dispensed, dosage history, existence of a fault condition, etc.), as well as physiological data of the patient.

In various embodiments, the patient programmer device may be physically coupled to a telemetry unit configured for wireless communication with the implantable drug delivery device. In embodiments, the patient programmer device may be removably coupled to the telemetry unit. The telemetry unit may be the same unit or a different unit than the telemetry unit used by the clinician mobile computing device for programming of the implantable drug delivery device. In some embodiments, the patient programmer device may be integral with the telemetry unit (i.e., it is not removably coupled to the telemetry unit). In some embodiments, the patient programmer may be a separate device, such as a mobile computing device (e.g., a phone, tablet computer, etc.) or a dedicated patient programmer unit having a feedback component and a patient input mechanism (e.g., a touchscreen display), useable by the patient and configured with software instructions to enable the device to receive and store parameters related to allowable modifications to a programmed drug delivery regimen, and to communicate with a separate telemetry unit to transmit instructions to modify the drug delivery regimen when authorized by the stored parameters.

Various embodiments are directed to a telemetry unit for an implantable drug delivery device. The telemetry unit may include a communication circuit for providing a communication interface with a mobile computing device, a transmitter/receiver component (e.g., a magnetic coil) for wireless signal communication with the implantable drug delivery device, and a processor and associated memory (e.g., a buffer) configured to provide a communication interface with the implantable drug delivery device.

The telemetry unit may further comprise a housing that may be coupled to a mobile computing device such that while the mobile computing device is coupled to the housing, the telemetry unit may establish a communication link with the mobile computing device. In some embodiments, the mobile computing device may be received by the housing and physically coupled to the telemetry unit during programming of an implantable drug infusion device, and may be removed from the housing after the implantable device is programmed.

In various embodiments, the telemetry unit may comprise a housing that may be coupled to a patient programmer component configured to enable a patient to selectively modify the drug delivery regimen of an implantable drug delivery device within parameters set by medical personnel. In some embodiments, the same telemetry unit may be used with both the mobile computing device during programming of the implantable drug infusion device and the patient programmer. For example, once the implantable drug delivery device is programmed and the mobile computing device is removed from the housing, a patient programmer component may be inserted into the housing. The patient programmer component may include, for example, a user input component (e.g., a button) and circuitry configured to detect a patient input event from the user input component (e.g., a button push) and to communicate an instruction to modify the drug delivery regimen (e.g., by administering a bolus dose) to the wireless transmitter/receiver component of the telemetry unit. The patient programmer component may also include a user feedback component, such as a display (e.g., an LCD screen, LED indicator(s), etc.) that may indicate whether or not a proposed user modification to the drug delivery regimen (e.g., a button push to request a bolus dose) was allowed and/or successfully implemented. The telemetry unit and/or the patient programmer component may further include communication circuitry configured to receive parameters related to allowable modifications to a programmed drug delivery regimen, a memory for storing the received parameters, and a processor, coupled to the memory for determining whether or not a proposed modification to the drug delivery regime corresponding to a detected patient input event (e.g., a button push) is allowed based on the stored parameters. When the proposed modification is allowed, the telemetry unit may transmit the instruction to the implantable drug delivery device.

In an alternative embodiment, the patient programmer component is not removable from the housing but may be an integral part of the telemetry unit.

In further embodiments, a first telemetry unit telemetry unit may comprise a housing adapted to receive a mobile computing device such that while the mobile computing device is received by the housing, the telemetry unit may establish a communication link with the mobile computing device for programming of the drug infusion device. A second telemetry unit may comprise a housing adapted to receive a patient programmer component configured to enable a patient to selectively modify the drug delivery regimen of an implantable drug delivery device within parameters set by medical personnel.

Various embodiments enable leveraging the flexibility, user-intuitiveness, processing power and networking capabilities of commonly-used mobile computing devices, such as mobile phones, tablet computers and PDA's, for programming and control of an implantable drug delivery system, while simplifying the requirements of dedicated electronic devices associated with such systems.

FIG. 1A illustrates a system 100 for programming an implantable drug delivery device 101 using a mobile computing device 301 according to one aspect of the invention. FIG. 1A schematically illustrates a patient 10 with an implantable drug delivery device 101 and an external telemetry unit 201 for communicating with the implantable drug delivery device 101 while it is inside the patient 10. The patient 10 may be a mammalian patient, such as a human.

The implantable drug delivery device 101 may communicate with the implantable drug delivery device over a wireless link 203. In one embodiment, the wireless link 203 uses a magnetic-based pulse position modulation (PPM) protocol, although other technologies and protocols could be utilized.

The implantable drug delivery device 101 may include a drug reservoir 103, a drug infusion pump 105, an internal controller 107 (e.g., a processor 109 and associated memory 111) that is configured to control the operation of the drug infusion pump 105, a wireless transceiver 113 for providing two-way communication between the internal controller 107 and the external telemetry unit 201, one or more sensors 115 that provide data to the controller 107 regarding conditions of the drug delivery device 101 and/or physiological conditions of the patient 10 (e.g., body temperature, heart rate, etc.), and a power source 117 (e.g., a battery), all of which may be housed in a biocompatible or bio-inert housing 119. The drug delivery device 101 further includes an outlet 121 for delivering metered doses of a drug to the patient 10, which may be via a delivery catheter 123 extending from the outlet 121 to one or more drug delivery sites 12 in target tissue.

The internal controller 107 controls the operation of the drug delivery device 101 by actuating the drug infusion pump 105, which may be a valve accumulator pump, based on control regimens (e.g., codes and commands) stored in memory 111 and executed by the processor 109 of the internal controller 107. The control regimens are executed to activate the drug infusion pump 105 so as to automatically dispense the drug from the drug reservoir 103 in accordance with a prescribed duration, flow rate or other parameters of drug delivery.

The internal controller 107 may also receive data from the sensors 115 and may use the sensor data to adjust, start or terminate the delivery of drugs. The manner in which the controller responds to sensor data may be prescribed by the stored control regimen.

The internal controller 107 may also be configured to receive a new, modified or updated drug delivery control regimen over the wireless link 203 from the external telemetry unit 201, and to store a received new, modified or updated drug delivery control regimen in the memory 111 of the controller 107. The controller 107 may then operate the drug infusion pump 105 to deliver the drug in accordance with the new, modified or updated control regimen. In this way, the implantable drug delivery device 101 may be programmed and/or re-programmed remotely over the wireless link 203, including when the device 101 is implanted in tissue of a patient 10. The internal controller 107 may also receive periodic commands from the patient 10 to modify the programmed drug delivery control regimen, such as by delivering a bolus dose of the drug to the patient, as described below. The internal controller 107 may also be configured to send data to another device over the wireless link 203, such as data related to the status of the device 101 (e.g., dosage history, amount of drug delivered and amount remaining in drug reservoir, remaining power, device malfunctions, etc.) and/or physiological data of the patient 10.

The telemetry unit 201 may be located external to the patient 10, and may include a wireless transmitter/receiver element 205, such as a magnetic coil, for communicating with the drug delivery device 101 over the wireless link 203. The telemetry unit 201 may include a housing 207 containing the transceiver 205 and associated circuitry, as well as a power supply 209 (e.g., one or more batteries). In embodiments, the telemetry unit 201 may be a portable unit that is designed to be maintained in close proximity to the patient 10 and within wireless range of the implanted drug delivery device 101, and may be, for example, carried or worn by the patient 10, or affixed to the skin of the patient 10.

The telemetry unit 201 may include a communication circuit 215 to provide a communication interface 217 with another device, such as the mobile computing device 301 shown in FIG. 1A. The communication interface 217 with the mobile computing device 301 may be via a physical (e.g., wire, cable, plug, etc.) connection, such as a USB connection. Alternatively or in addition, the interface 217 may be a wireless interface, including a short-range wireless interface, such as a Personal Area Network (PAN) interface using a IEEE 802.15x standard (e.g., a BLUETOOTH® interface), or a near-field wireless interface. The telemetry unit 201 may further include a control processor 211 and memory 213 (e.g., an input/output buffer) to provide modulation and demodulation of signals sent to and from wireless transmitter/receiver 205. Thus, in various embodiments, the telemetry unit 201 may provide a bridge for communication between the implantable drug delivery device 101 and a mobile computing device 301, such that that the mobile computing device 301 may communicate with and program the implantable drug delivery device 101, as described below.

The telemetry unit 201 may be configured to be physically coupled to the mobile computing device 301. For example, the housing 207 of the telemetry unit 201 may include an opening 219, such as a cavity, slot, recess, cradle, etc., that may be configured to receive the mobile computing device 301 such that the mobile computing device 301 may be physically coupled to the telemetry unit 201. In some embodiments, the telemetry unit 201 may include one or more features that may be configured to be received in an opening in the mobile computing device 301 to physically couple the mobile computing device 301 to the telemetry unit 201. For example, the housing 207 of the telemetry unit 201 may include a plug, such as a USB plug, that may plug into a USB port on the mobile computing device 301. As discussed above, in various embodiments the communication interface 217 between the mobile computing device 301 and the telemetry unit 201 may be a short-range interface (e.g., 10 meters or less, such as 5 meters or less), and in the case of a near-field interface or a physical connector interface, the devices may need to be in relatively close proximity (e.g., ~5 cm or less), or even physically contacting each other, in order to establish a connection. This may serve an important safety function, since requiring the devices to be in relatively close proximity to establish a connection may minimize the possibility that the mobile computing device 301 will unintentionally establish a connection with any telemetry unit other than the telemetry unit 201 associated with the implantable drug delivery device 101 to be programmed. Providing a physical coupling between the mobile computing device 301 and the telemetry unit 201 during programming of the implantable device 101 helps ensure that the mobile computing unit 301 and telemetry unit 201 establish a robust connection for transfer of programming and other data that will not be interrupted during the programming of the implantable device 101.

The system 100 may also include a mobile computing device 301 configured to program the implantable infusion device 101. The mobile computing device 301 may be a typical portable computing device (e.g., smartphone, tablet, etc.) with communication capabilities for transmitting and receiving data over a communication network 303, such as a cellular telephone network, a radio access network, a WiFi network, a WiMAX network, etc. In one example, as shown in FIG. 1A, the communication network 303 is a cellular telephone network that includes a plurality of access points 305 (e.g., base stations) coupled a network operations center 308 which may operate with other network infrastructure (e.g., servers, routers, etc., not shown) to connect the mobile computing device 301 to other network destinations, such as a server 331, which may be via telephone land lines (e.g., a POTS network, not shown) and/or the Internet 307. Communications between the mobile computing device 301 and the communication network 303 may be accomplished via a two-way wireless communication link 309, which may use 4G, 3G, CDMA, TDMA, LTE and/or other technologies.

Alternatively or in addition, the communication network 303 may be a local area network (LAN) or campus network, such as a private hospital network. The mobile computing device 301 may communicate with network access point(s) 305 via a short or medium range wireless communication link, such as a IEEE 801.11 standard (e.g., WiFi) or BLUETOOTH® link. The network 303 may optionally provide access to an external wide-area network (WAN), such as the Internet 307.

Figure 2:
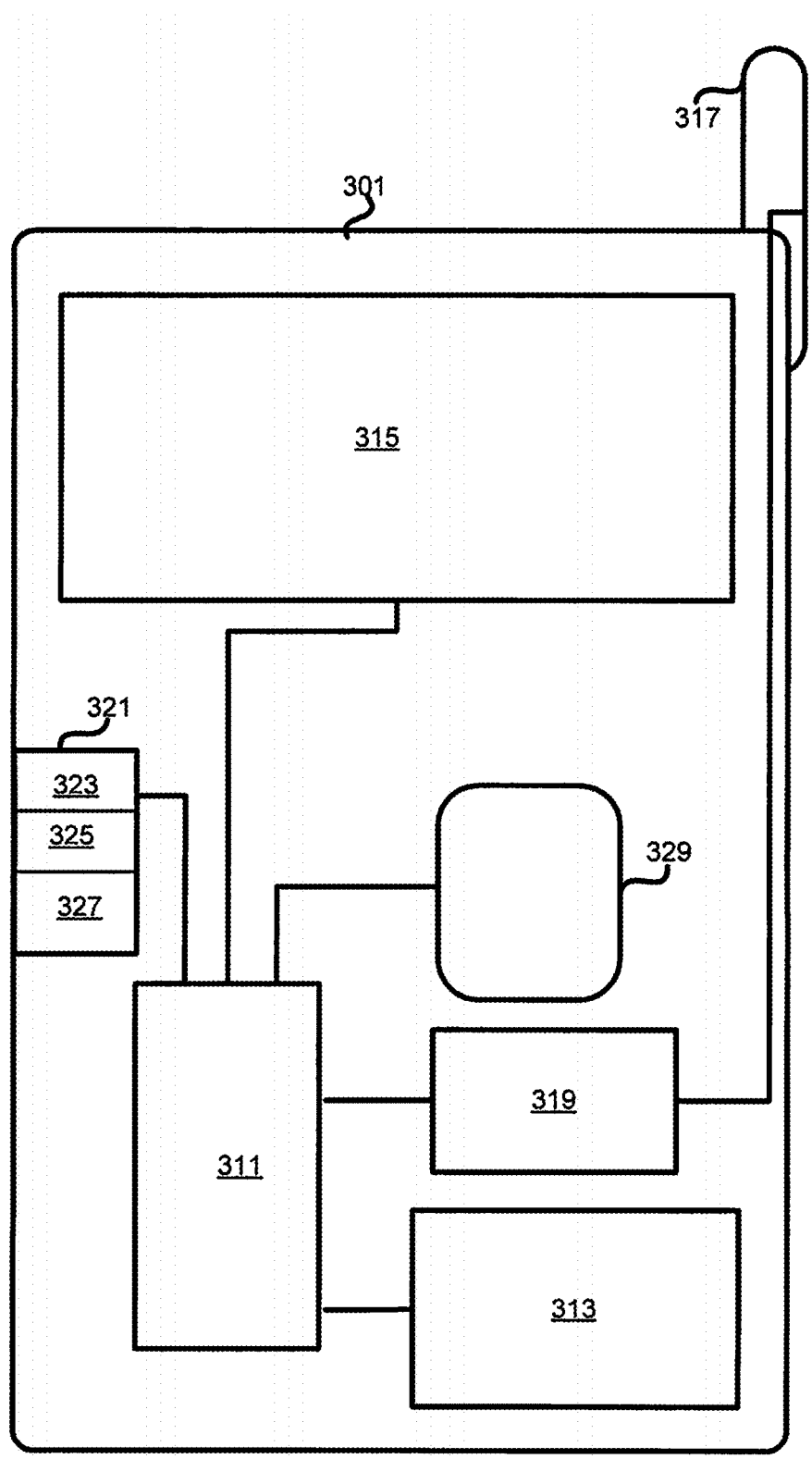
FIG. 2 is a system block diagram of a mobile computing device usable in various embodiments.

A typical mobile computing device 301 for use in the various embodiments may include the components illustrated schematically in FIG. 2. For example, mobile computing device 301 may include a processor 311 coupled to internal memory 313 and to a display 315. Additionally, the mobile computing device 301 may have an antenna 317 for sending and receiving electromagnetic radiation that is connected to a wireless data link and/or cellular telephone transceiver 319 coupled to the processor 311. In some embodiments, the transceiver 319 and portions of the processor 311 and memory 313 used for cellular telephone communications may be collectively referred to as the air interface. The mobile computing device 311 may further include one or more additional communication modules 321, 323, 325 coupled to the processor 311, such as a USB communication module 321, which may include a USB port and associated control circuitry, a PAN communication module 323, which may include a wireless PAN (e.g., BLUETOOTH®) transmitter/receiver and associated control circuitry, and a near-field communication (NFC) module 325, which may include a NFC transmitter/receiver and associated control circuitry. The mobile computing device 301 may also include a user input component 327 coupled to the processor 311, which may be, for example, a touchscreen user interface, a keypad and/or one or more buttons or switches.

The processor 311 may be any programmable microprocessor, microcomputer or multiple processor chip or chips that can be configured by software instructions (applications) to perform a variety of functions. In some devices, the processor 311 may include internal memory sufficient to store the application software instructions. In many mobile computing devices, the internal memory 313 may be a volatile or nonvolatile memory such as flash memory, or a mixture of both. For the purpose of this description, a general reference to memory includes all memory accessible to the processor 311, including internal memory 313, removable memory plugged into the mobile computing device, and memory within the processor 313 itself.

The system 100 may also include a patient programmer unit 401, as shown in FIG. 1A. The patient programmer unit 401 may be usable by the patient 10 to selectively modify the drug delivery regimen of an implantable drug delivery device 101 within parameters set by a physician or other medical clinician. In some embodiments, the patient programmer unit 401 may be a simple, easy-to-use device with limited functionality, such as functionality to enable a patient to administer an extra dose (i.e., a bolus dose) of the drug when needed.

As schematically illustrated in FIG. 1A, the patient programmer unit 401 may include an internal controller 403 (e.g., a processor 405 and associated memory 407), a user input component 409 coupled to the controller 403, and a display 411 coupled to the controller 403. The user input component 409 may be as simple as a button that a user may push to request the administration of a bolus dose of medication. Other more complex user input components can also be utilized. Similarly, the display 411 may be a relatively simple, low-cost display, such as an LCD screen, LED indicator(s), and/or audio alarm(s), that provides the patient with feedback regarding the operations of the patient programmer unit 401, such as whether or not request for a bolus dose is successful.

In some embodiments, the patient programmer unit 401 may resemble a typical mobile communication device (e.g., a smartphone) but with limited functionality. For example, the display 411 of the patient programmer unit 401 may be a touchscreen display that may also function as a user input component 409. The patient programmer unit 401 may also include additional input component(s) 409, such as one or more hard keys, switches, buttons, etc. In some embodiments, the user input component 409 may comprise circuitry that detects a user input event external to the patient programmer unit 401, such as a push of a button or hard key located on the telemetry unit 201. The patient may use the patient programmer unit 401 to selectively modify the drug delivery regimen of the implantable drug delivery device 101 within prescribed parameters (e.g., request a bolus dose) as well as to display information regarding the implantable drug delivery device and/or the programmed drug delivery regimen, such as current status data or historical data of the device (e.g., amount of drug dispensed and remaining to be dispensed, dosage history, existence of a fault condition, etc.), and physiological data of the patient when such data is available.

The patient programmer unit 401 may also include a communication module 413 coupled to the processor 405 that enables the patient programmer unit 401 to communicate with at least one other device. For example, the communication module 413 may enable the patient programmer unit 401 to establish a wired (e.g., USB) or wireless (e.g., near-field communication (NFC), personal area network (PAN) communication such as BLUETOOTH®, etc.) communication link 415 with the telemetry unit 201 for transmitting commands to the telemetry unit 201 (e.g., in response to a button push) for relay to the implantable drug delivery device 101. The patient programmer 401 may also receive feedback from the telemetry unit 201 regarding the status of a command (e.g., whether it was successfully transmitted to the implantable device 101, whether a requested bolus dose was successfully administered, etc.). The communication module 413 may also establish a wired or wireless communication link 417 with the mobile computing device 301 for programming of the patient programmer unit 401. In some embodiments, the patient programmer unit 401 may include an antenna and transceiver, such as shown in FIG. 2, and may be capable of communicating with distant servers 331 and/or making a connection with the Internet 300 via a wireless telecommunication network 303 (e.g., via wireless communications with a network 305, 308).

The controller 403 of the patient programmer unit 401 may be configured to receive parameters related to allowable modifications to a programmed drug delivery regimen, and to store such received parameters in memory 407. The parameters may include, for example, a total number of bolus doses that may be requested by the patient, the number of bolus doses that may be requested in a given time period, a minimum wait time between successive requests for bolus doses, the volume of each bolus dose, etc. When the patient 10 inputs a request to modify the programmed drug delivery regimen (e.g., by requesting a bolus dose), the processor 405 of the patient programmer device 401 may be configured to either allow or deny the request, in accordance with the parameters stored in memory 407, and to indicate on the display 411 whether the request was allowed.

The patient programmer unit 401 may be configured to be physically coupled to the telemetry unit 201. In some embodiments, the patient programmer unit 401 may be sized and shaped so as to be received in the opening 219 of the housing 207 of the telemetry unit 201. Thus, after the mobile computing device 301 is finished programming the implantable drug delivery device 101, the mobile computing device 301 may be removed from the housing 207 of the telemetry unit 201 and the patient programmer unit 401 may be inserted into the opening 219 of the housing 207. The patient programmer unit 401 may be programmed with patient-modification parameters by the mobile computing device 301 at any time during the programming process, including either before or after the patient programmer unit 401 is placed into the opening 219 of the telemetry unit housing. After programming is complete, the patient programmer unit 401, coupled to the telemetry unit 201, may be provided to the patient 10 and used by the patient to request modifications to the programmed drug delivery regimen, in accordance with the stored patient modification parameters.

Figure 1B:
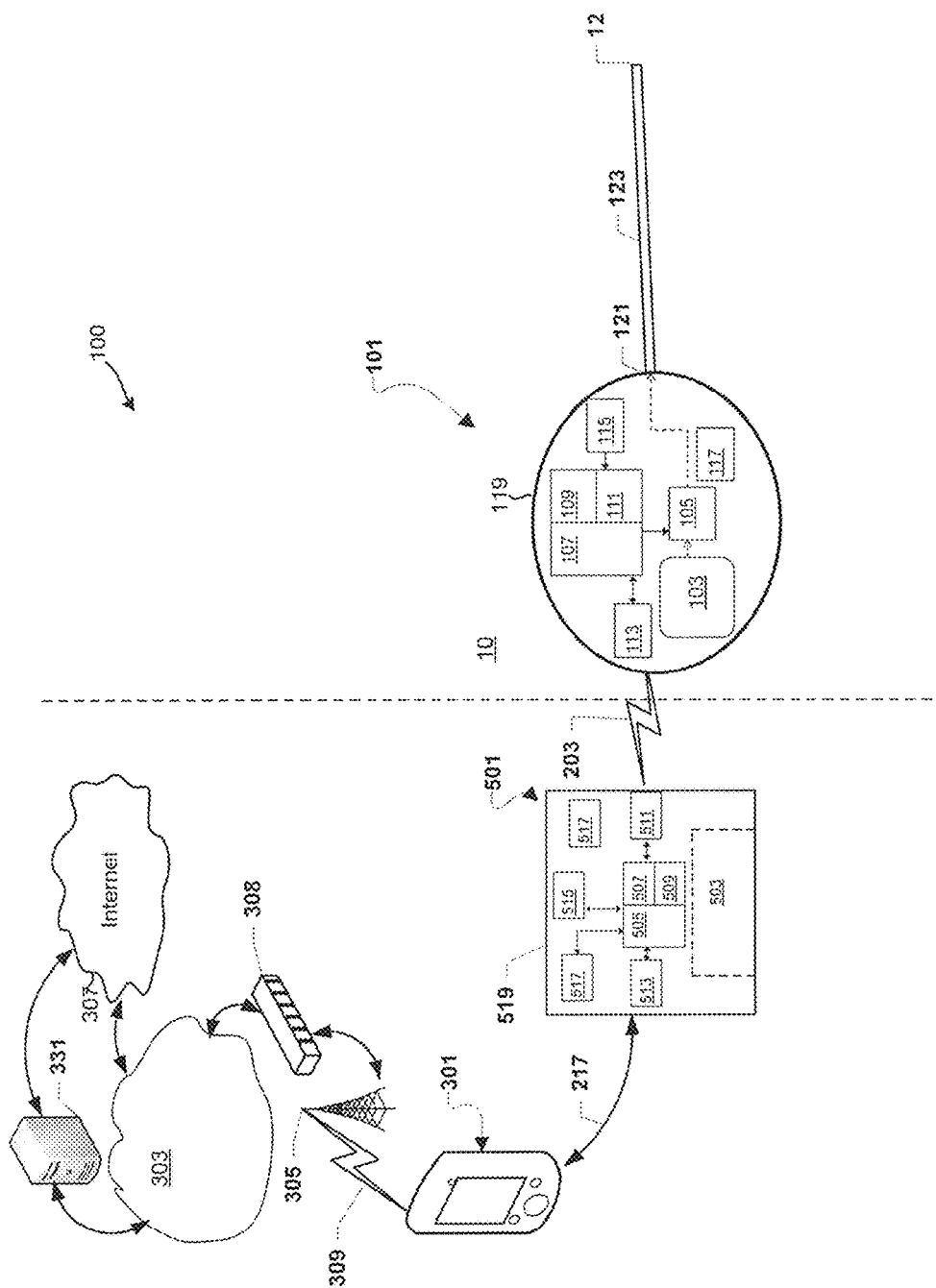
FIG. 1B is a schematic diagram of a system for programming and controlling an implantable drug delivery device using a mobile computing device and a combined patient programmer/telemetry unit.

In an alternative embodiment, the telemetry unit 201 and patient programmer unit 401 may be combined into an integrated patient programmer/telemetry unit 501, as shown in FIG. 1B. In this embodiment, a mobile computing device 301 may be coupled to the combined patient programmer/telemetry unit 503, such as by being received in an opening 503 of the combined patient programmer/telemetry unit 503, for programming of both the implantable drug delivery device 101 and the patient programmer component of the combined patient programmer/telemetry unit 501.

The combined patient programmer/telemetry unit 501 may include a transmitter/receiver element 511 for communicating with the implantable drug delivery device 101 via wireless link 203, a controller 505, which may include a processor 507 and memory 505, and a communication module 513 for establishing a wired or wireless link 217 with a mobile computing device 301 for programming of the implantable drug delivery device 101 and for programming of patient modification parameters, which may be stored in the memory 505 of the unit 501. The unit 501 may also include a user input component 513 to enable the patient 10 to request a patient modification to the drug delivery regimen (e.g., a bolus dose) and a display 515 to display a status of the unit 501. All these components may be housed in a common housing 519, which may also include an internal power supply 517 (e.g., a battery).

Figure 1C:
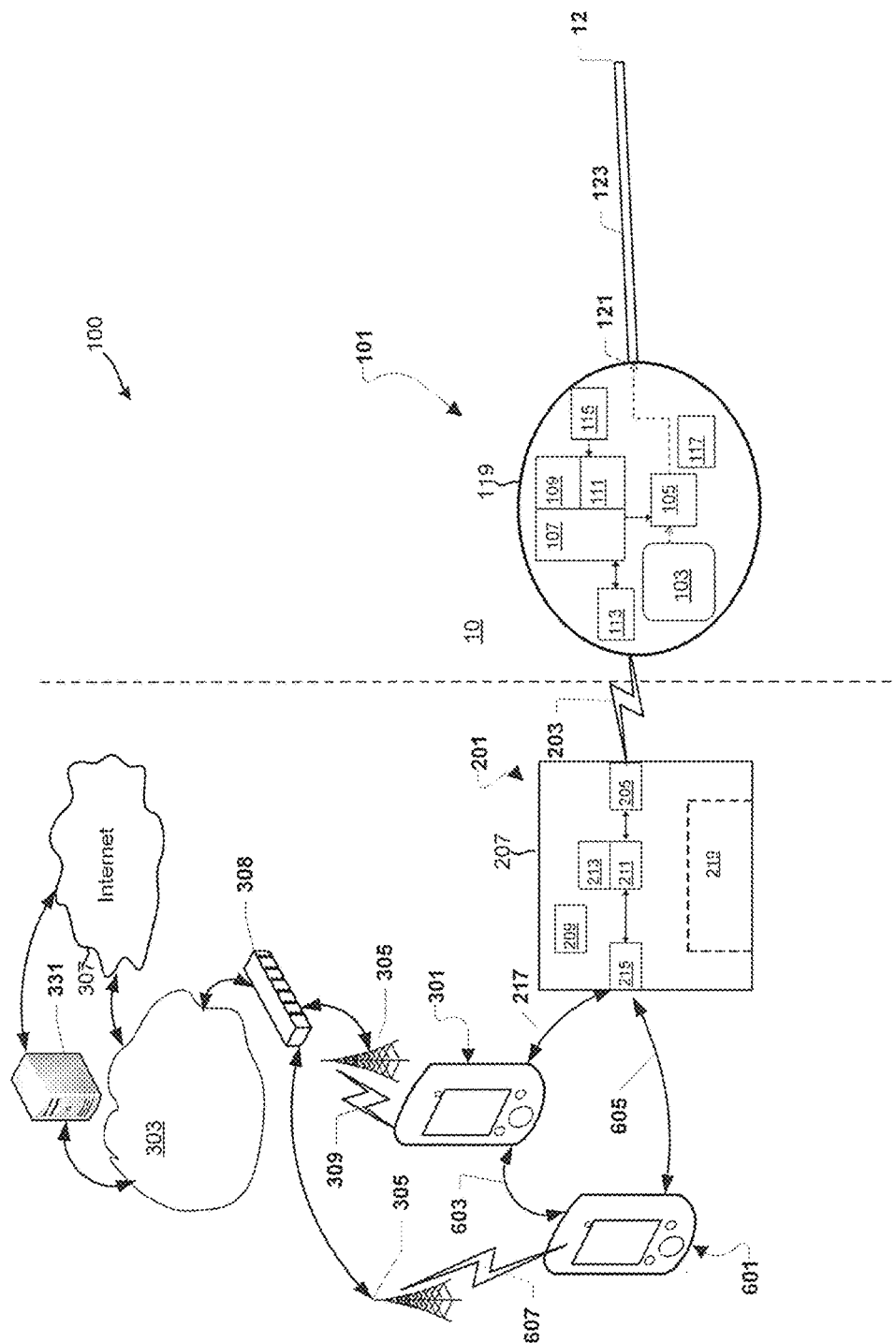
FIG. 1C is a schematic diagram of a system for programming and controlling an implantable drug delivery device using a first and second mobile computing device and a telemetry unit.

In yet another alternative embodiment, the above-described patient programmer functionality may not be provided by a dedicated device, such as patient programmer unit 401 shown in FIG. 1A, but may instead be provided by a second mobile computing device 601, as shown in FIG. 1C. The second mobile computing device 601 may be a typical portable computing device (e.g., smartphone, tablet, etc.) that may include the components illustrated in FIG. 2.

The second mobile computing device 601 may be configured with software (e.g., application software) to enable the patient to selectively modify the drug delivery regimen of an implantable drug delivery device 101 within parameters set by a physician or other medical clinician. The parameters may be received from the first mobile computing device 301 and stored in the memory of the second device 601. The parameters may be received over a wired or wireless link 603 between the first and second mobile computing devices 301, 601. In some embodiments, the parameters or updated parameters may be received remotely over a link 607 with communications network 303. The parameters may be received from the first mobile computing device 301 or from another network 303 resource or node, including from the Internet 307. The second wireless computing device 601 may be configured to provide a wired or wireless link 605 to the telemetry unit 201 for transmitting instructions to modify the programmed drug delivery regimen (e.g., by administering a bolus dose) to the implantable drug delivery device 101. Executable software on the second mobile computing device 601, which may be downloaded to the device 601 over communication network 303, may enable the patient 10 to input requests to modify the programmed drug delivery regimen via the user interface of the second mobile computing device 601. The second mobile computing device 601 may be physically coupled to the telemetry unit 201, such as by being inserted into an opening 219 in the housing 207 of the telemetry unit 201, to help ensure a robust connection between the second mobile computing device 601 and the telemetry unit 201 for communicating patient requests to the implantable drug delivery device 201.

In some embodiments, the second mobile computing device 601 may be used to program the implantable drug delivery device 101 with a new or updated drug delivery regimen. The drug delivery regimen may be received at the second mobile computing device 601 over the network 303, and may be received from another device, such as first mobile computing device 301, used by a physician or other medical professional. The received drug delivery regimen may be transmitted from the second mobile computing device 601 to the implantable drug delivery device 101 for programming of the device 101 via the telemetry unit 201.

Figure 1D:
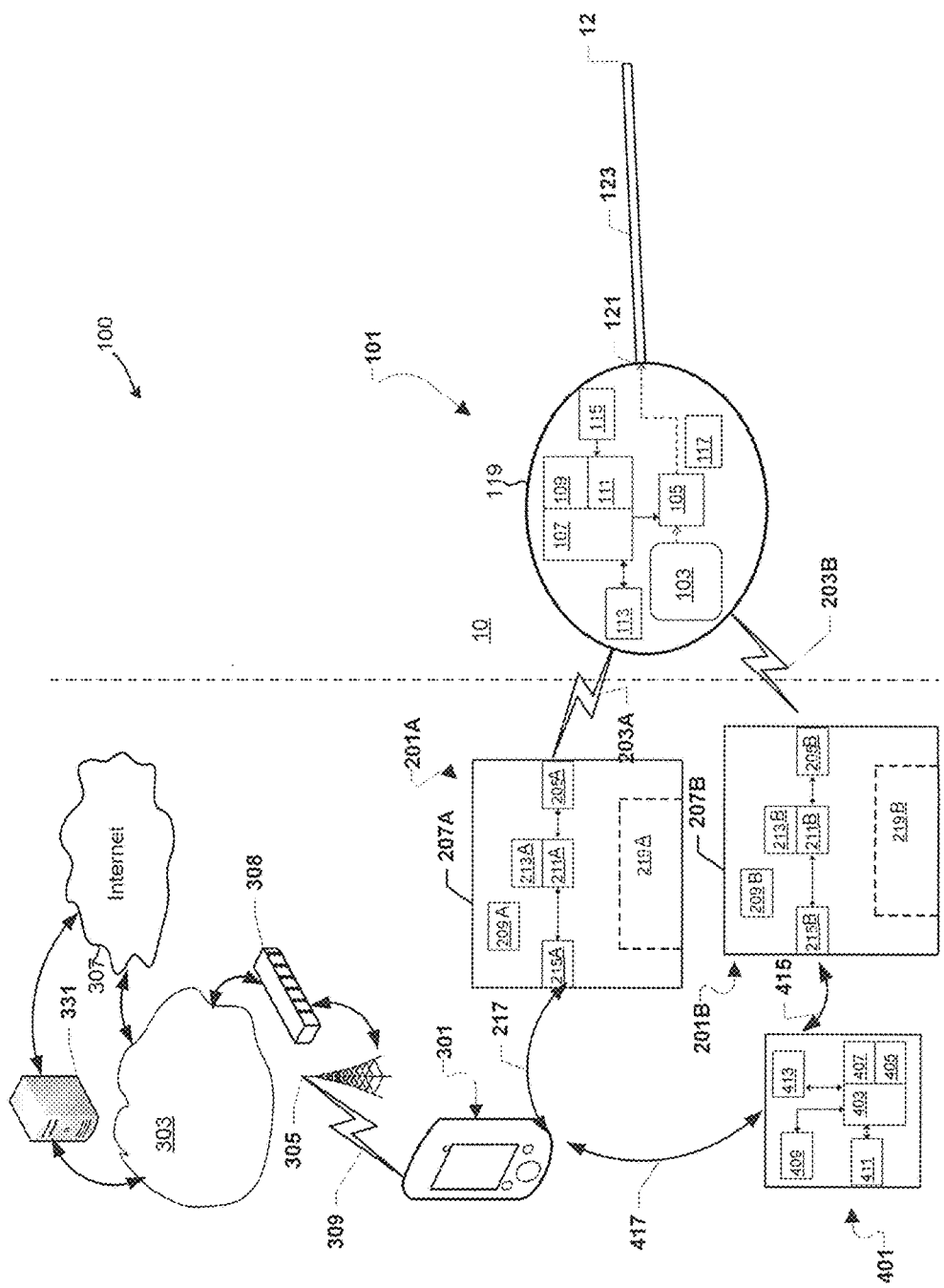
FIG. 1D is a schematic diagram of a system for programming and controlling an implantable drug delivery device using a mobile computing device that interfaces with a first telemetry unit and a patient programmer that interfaces with a second telemetry unit.

In yet another alternative embodiment, two separate telemetry units 201A, 201B may be utilized as shown in FIG. 1D. Each telemetry unit 201A, 201B may be similar to the telemetry unit 201 described above in connection with FIG. 1A. A first telemetry unit 201A may have a communication circuit 215A configured to provide a communication interface 217 with the mobile computing device 301 for programming of the implantable drug infusion device 101 as described above. The housing 207A of the first telemetry unit 201A may include an opening 219A that is configured to receive the mobile computing device 301 such that the mobile computing device 301 may be physically coupled to the telemetry unit 201. The second telemetry unit 201B may have a communication circuit 215B to provide a communication interface 415 with the patient programmer unit 401 to enable the patient to request modifications to the programmed drug delivery regimen as described above. A housing 207A of the second telemetry unit 201B may include an opening 219B that is configured to receive the patient programmer unit 401 such that the patient programmer unit 401 may be physically coupled to the second telemetry unit 201B. Alternately, the patient programmer unit 401 may be integral with the second telemetry unit 201B.

Figure 3:
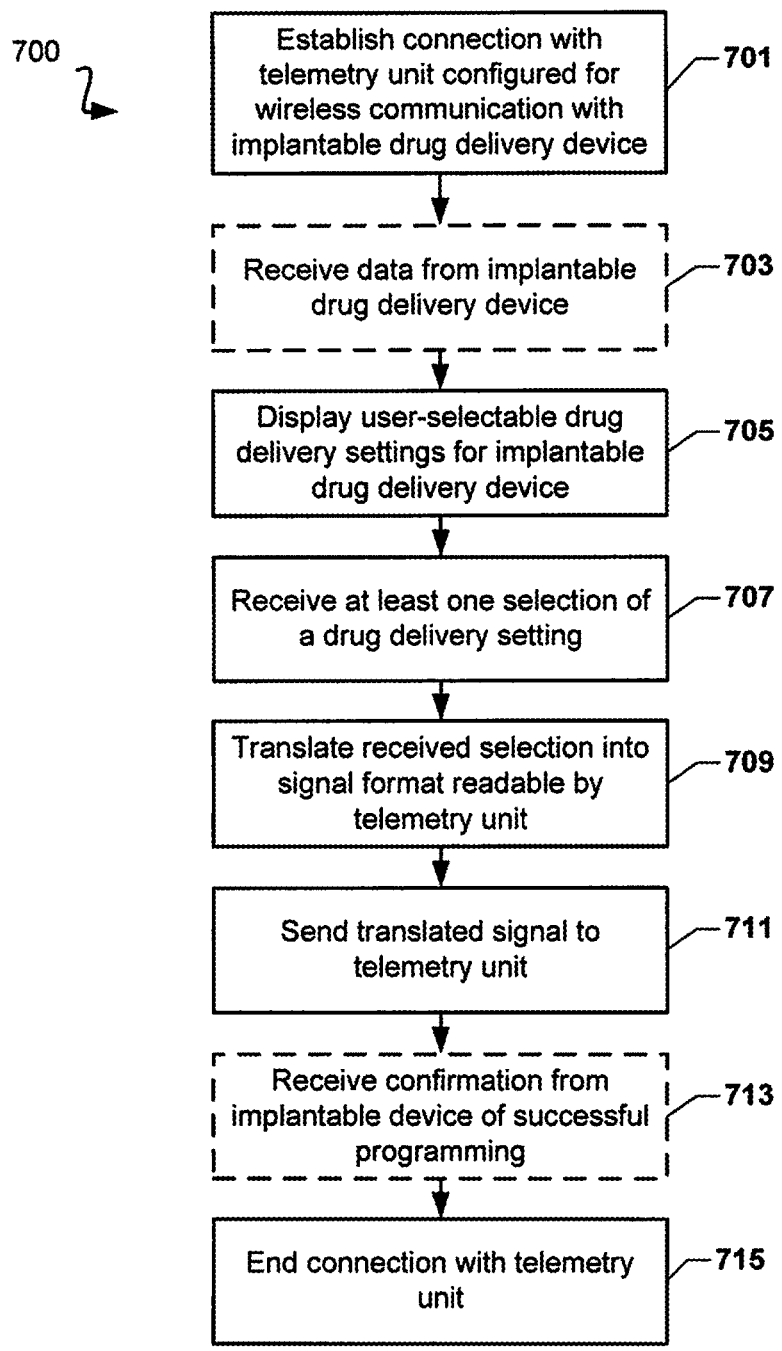
FIG. 3 is a process flow diagram illustrating an embodiment method for programming an implantable drug delivery device using a mobile computing device.

FIG. 3 is a process flow diagram illustrating an embodiment method 700 for programming an implantable drug delivery device, such as device 101 shown in FIGS. 1A-D. The method 700 may be performed by a mobile computing device 301, such as shown in FIGS. 1A-2, and in particular by a processor 311 of a mobile computing device 301 that is configured with processor-executable software instructions that may be stored in a memory 313 of the device. The software instructions may be application software that may be downloaded to the mobile computing device 301 over a communications network (e.g., network 303 and/or Internet 307 in FIGS. 1A-D), and may be downloaded from a server 331. In various embodiments, a downloadable version of application software allows general purpose computing devices to download and run the software that provides functionality for programming of implantable drug delivery devices. In other embodiments, the mobile computing device 301 may have factory-installed application software for supporting the device programming functions.

In block 701 of method 700, the mobile computing device 301 may establish a connection with a telemetry unit configured for wireless communication with an implantable drug delivery device. As shown in FIGS. 1A-D, for example, the mobile computing device 301 may establish a connection to the telemetry unit 201, 501, 201A via a wired or wireless link 217, such as via a USB connection, a wireless PAN (e.g., BLUETOOTH®) connection, or a near field communication (NFC) connection. The establishing of a connection with the telemetry unit may occur substantially simultaneously with a physical coupling of the mobile computing device 301 and the telemetry unit, such as by placing the mobile computing device 301 within an opening 219, 503, 219A of the telemetry unit 201, 501, 201A.

The establishing of a connection with the telemetry unit may optionally include an authentication process to ensure that the mobile computing device 301 and/or the user of the device 301 is authorized to communicate with and program the implantable drug delivery device 101. For example, the mobile computing device 301 may provide credentials (e.g., an identifier, security key, password, etc.) to the telemetry unit 201, 501, 201A and/or to the implantable device 101 which may be checked by logic on the telemetry unit 201, 501, 201A or the implantable device 101 to ensure that the mobile device 301 and/or the user of the device, which is typically a physician or other medical professional, is authorized to program the device. In embodiments, the authentication process, or portions thereof, may be performed remotely over the communication network 303. For example, the mobile computing device 301 may communicate over the network 303 with a server 331, and may provide the server 331 with identifying information regarding the mobile computing device 301 and/or the user of the device, as well as identifying information regarding the implantable device 101 and/or the patient 10. The server 331 may be configured to access a database to determine whether the mobile computing device 301 and/or the user of the device 301 is authorized to program the drug delivery device 101 implanted in the patient 10. When the mobile device 301 and user are authorized, the server 331 may transmit authorization data, which could include a security key, a software plug-in, etc., that enables the programming of the implantable device 101 to proceed.

In optional block 703 of method 700, the mobile computing device 301 may receive data from the implantable drug delivery device 101. The data may be sent from the implantable drug delivery device 101 to the telemetry unit 201, 501, 201A via wireless connection 203, and passed to the mobile computing device 301 over the connection 217 with the telemetry unit 201, 501, 201A. The data may relate to the status of the implantable drug delivery device 101 (e.g., dosage history, amount of drug delivered and amount remaining in drug reservoir, remaining power, device malfunctions, etc.) and/or physiological data of the patient 10, which may be useful to the physician when programming the implantable device 101 with a new or updated drug delivery regimen.

In block 705 of method 700, the mobile computing device 301 may display user-selectable drug delivery settings for the implantable drug delivery device 101. The user-selectable settings may be displayed in a graphical user interface on a display screen of the mobile computing device 301, for example. In embodiments, the application software running on the mobile computing device 301 may be configured to walk the physician through the process of creating a new or modified drug delivery regimen for the patient. At least one selection of a drug delivery setting may be received at block 707. The drug delivery settings may be entered by a physician or other authorized clinician using the user interface component of the mobile computing device 301, which may be a touchscreen interface, a keypad, or the like. The at least one selection of a drug delivery setting may comprise a new or updated drug delivery regimen.

In block 709, the received selection(s) may be translated into a signal format that is readable (i.e., able to be understood) by the telemetry unit 201, 501, 201A. In block 711, the translated signals corresponding to the received selection(s) are sent to the telemetry unit 201, 501, 201A. The telemetry unit 201, 501, 201A may then forward the signals over the wireless link 203, 203A to the implantable drug delivery device 101 for programming of the device 101.

In optional block 713, the mobile computing device 301 may receive confirmation from the implantable drug delivery device 101 that the device 101 has been successfully programmed. The confirmation message may be sent from the implantable drug delivery device 101 to the telemetry unit 201, 501, 201A via wireless connection 203, 203A and passed to the mobile computing device 301 over the connection 217 with the telemetry unit 201, 501, 201A. Additionally, the telemetry device 201, 501, 201A and/or the implantable drug delivery device 101 may send a message indicating that an attempted programming failed.

Following programming of the implantable drug delivery device 101, the connection between the mobile computing device 301 and the telemetry unit 201, 501, 201A may be ended in block 715. The mobile computing device 301 may be physically de-coupled from the telemetry unit 201, 501, 201A. The implantable drug delivery device 101 may deliver drug(s) to the patient in accordance with the programmed drug delivery regimen.

As described above and illustrated in FIGS. 1A-1D, the mobile computing device 301, which is configured to provide a programming interface with the telemetry unit 201, may be capable of communicating with distant servers 331 and making a connection with the Internet 300 via a wireless telecommunication network 303 (e.g., via wireless communications 309 with a cellular network 305, 308). Thus, once the mobile computing device 301 has established a connection with a patient programmer 401 (e.g., FIG. 1A) or a combined patient programmer/telemetry unit 501 (e.g., FIG. 1B) in block 701, data from the patient programmer and/or telemetry unit may be relayed via the wireless telecommunication network 303 in block 703 to a computing device of a physician at a remote location for display in block 705. For example, a physician may login to a website hosted by a server 331 that enables the physician to receive information relayed by the mobile computing device 301, such as current user-selectable drug delivery settings. Further information that may be relayed to a physician's computing device at a remote location may include patient vital signs as may be sensed by the implantable drug delivery device 101, fluid levels of one or more reservoirs within the implantable drug delivery device 101, and/or electronic status and diagnostic information that may be relayed by the implantable drug delivery device 101.

Using the network accessibility provided by the mobile computing device 301 and telecommunication networks, a physician and a remote location may interact with a display of programming options for the patient programmer, such as interacting with the website hosted by a server 331. Thus, the mobile computing device 301 may receive selections of drug delivery settings from the physician in block 707 via communications from a distant computer (e.g., the Internet). This capability enables physicians to remotely diagnose, reprogram and otherwise manage the patient's implantable drug delivery device 101 and/or patient programmer 201, 401, 501 without requiring the patient to come to the doctor's office. In many situations, this capability may enable faster and more effective care than possible with devices that must be programmed locally.

Figure 4:
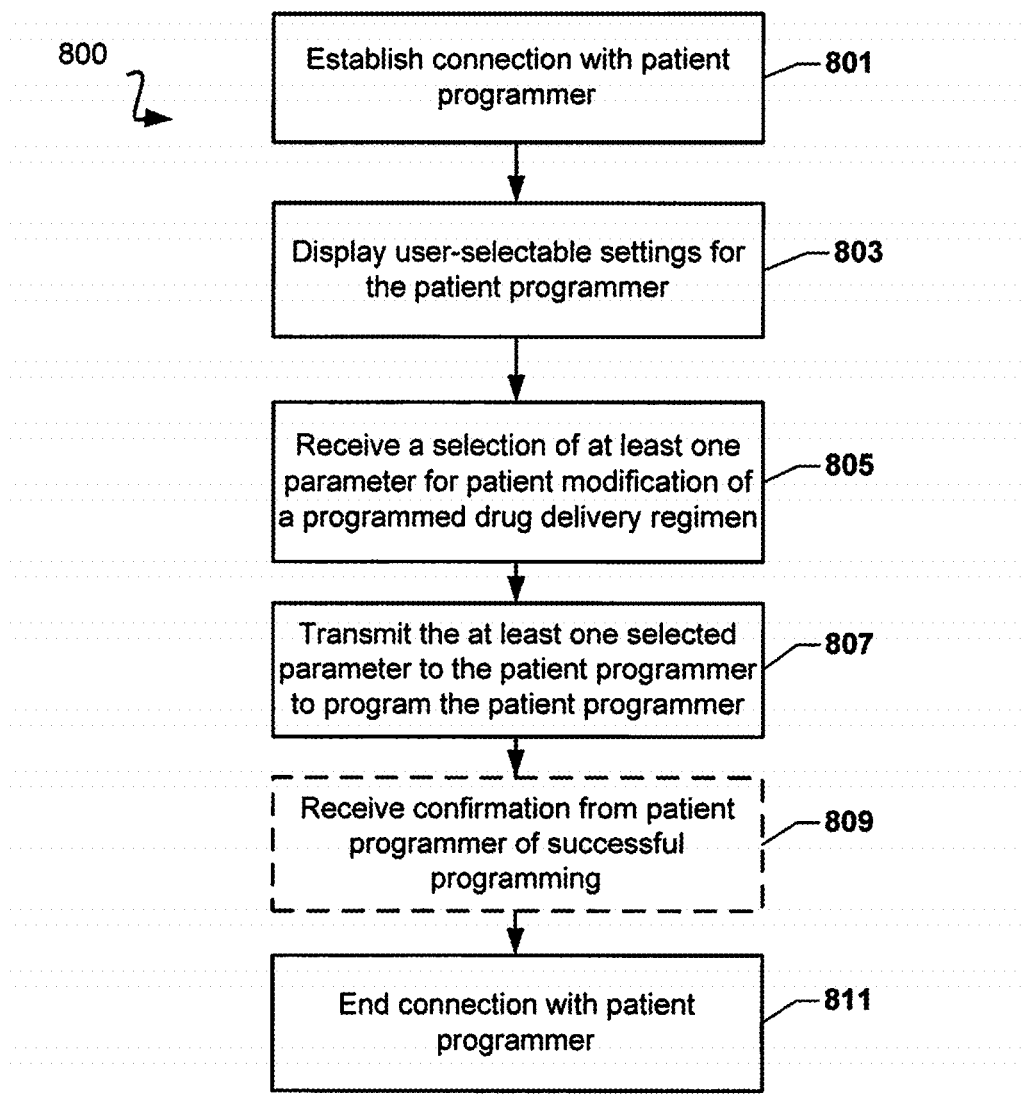
FIG. 4 is a process flow diagram illustrating an embodiment method for programming a patient programmer using a mobile computing device.

FIG. 4 is a process flow diagram illustrating an embodiment method 800 for programming a patient programmer unit, such as a patient programmer unit 401 as shown in FIGS. 1A and 1D, a combined patient programmer/telemetry unit 602 as shown in FIG. 1B, or a mobile computing device 601 configured with patient programmer functionality as shown in FIG. 1C. The method 800 may be performed by a mobile computing device 301, such as shown in FIGS. 1A-D, and in particular by a processor 311 of a mobile computing device 301 that is configured with processor-executable software instructions that may be stored in a memory 313 of the device, as schematically shown in FIG. 2. The software instructions may be application software that may be downloaded to the mobile computing device 301 over a communications network (e.g., network 303 and/or Internet 307 in FIGS. 1A-D), and may be downloaded from a server 331. In various embodiments, a downloadable version of application software allows general purpose computing devices to download and run the software that provides functionality for programming of patient programmer devices. In other embodiments, the mobile computing device 301 may have factory-installed application software for supporting the programming functions. The software for performing the method 800 of FIG. 4 may be the same as or different from software for programming an implantable drug delivery device, such as described above in connection with method 700 of FIG. 3.

In block 801 of method 800, the mobile computing device 301 may establish a connection with a patient programmer, such as patient programmer unit 401 shown in FIGS. 1A and 1D, combined patient programmer/telemetry unit 501 shown in FIG. 1B or a second mobile computing device 601 configured with a patient programmer functionality as shown in FIG. 1C. The mobile computing device 301 may establish a connection to the patient programmer via a wired or wireless link 415, 217, 603 such as via a USB connection, a wireless PAN (e.g., BLUETOOTH®) connection, or a near field communication (NFC) connection. In embodiments in which the patient programmer is network enabled, the mobile communication device 301 may establish the connection via a telecommunications network 303 and/or the Internet 307.

The establishing of a connection with the patient programmer may optionally include an authentication process to ensure that the mobile computing device 301 and/or the user of the device 301 is authorized to communicate with and program the patient programmer 401, 501, 601. For example, the mobile computing device 301 may provide credentials (e.g., an identifier, security key, password, etc.) to the patient programmer 401, 501, 601 which may be checked by logic on the patient programmer 401, 501, 601 to ensure that the mobile device 301 and/or the user of the device 301, which is typically a physician or other medical professional, is authorized to program the patient programmer with parameters for patient modification of a drug delivery regimen. In embodiments, the authentication process, or portions thereof, may be performed remotely over the communication network 303. For example, the mobile computing device 301 may communicate over the network 303 with a server 331, and may provide the server 331 with identifying information regarding the mobile computing device 301 and/or the user of the device, as well as identifying information regarding the patient programmer 401, 501, 601 and/or the patient 10. The server 331 may be configured to access a database to determine whether the mobile computing device 301 and/or the user of the device 301 is authorized to program the patient programmer 401, 501, 601 with parameters for patient modification of a drug delivery regimen. When the mobile device 301 and user are authorized, the server 331 may transmit authorization data, which could include a security key, a software plug-in, etc., that enables the programming of the patient programmer 401, 501, 601 to proceed.

In block 803 of method 800, the mobile computing device 301 may display user-selectable settings for the patient programmer. The user-selectable settings may be displayed in a graphical user interface on a display screen of the mobile computing device 301, for example. In embodiments, the application software running on the mobile computing device 301 may be configured to lead the physician through the process of setting parameters for patient modification to a programmed drug delivery regimen stored in an implantable drug delivery device 101. For example, the parameters may relate to the number of bolus doses of a drug that a patient may request in a predetermined time period, the volume of drug administered per bolus, a minimum wait time between administering bolus doses, time(s) of day in which bolus doses may be administered, an allowable modification to a basal rate of drug delivery that a patient may request, etc. The user of the mobile computing device 301 may enter various parameters relating to allowable patient modifications, and a selection of at least one parameter for patient modification of a programmed drug delivery regimen may be received at block 805. The selection may be entered using the user interface component of the mobile computing device 301, which may be a touchscreen interface, a keypad, or the like.

In block 807, the selected parameter(s) may be transmitted to the patient programmer 401, 501, 601 to program the patient programmer with the selected parameter(s). In embodiments, the selected parameter(s) may be transmitted directly to the patient programmer 401, 501, 601 via a link 415, 217, 603. In other embodiments, the selected parameter(s) may be transmitted to another device, such as the telemetry unit 201 or the implantable drug delivery device 101. The selected parameter(s) may be transmitted while the mobile computing device 301 programs the implantable device 101, for example. The parameter(s) may be stored at least temporarily on the other device and later sent to the patient programmer.

In optional block 809, the mobile computing device 301 may receive confirmation from the patient programmer 401, 501, 601 that the patient programmer has been successfully programmed. Additionally, the patient programmer 401, 501, 601 may send a message indicating that an attempted programming failed.

Following programming of the patient programmer 401, 501, 601, the connection between the mobile computing device 301 and the patient programmer 401, 501, 601 may be ended in block 811. The patient programmer 401, 501, 601 may be used to modify a programmed drug delivery regimen of the implantable drug delivery device 101 in accordance with the parameters programmed by the mobile computing device 301.

Figure 5:
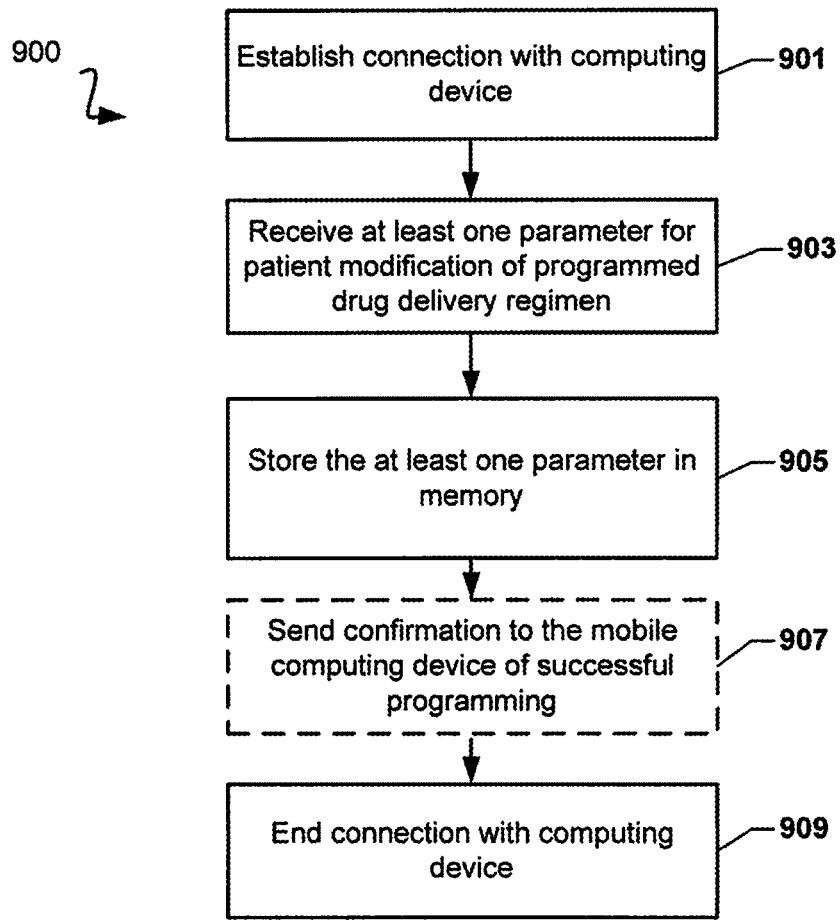
FIG. 5 is a process flow diagram illustrating an embodiment method of programming a patient programmer with parameters for user modification of a programmed drug delivery regimen.

FIG. 5 is a process flow diagram illustrating an embodiment method 900 of programming patient modification parameters. The method 900 may be performed in parallel with method 800 shown in FIG. 4. The method 900 of FIG. 5 may be performed by a patient programmer, such as a patient programmer unit 401 as shown in FIGS. 1A and 1D, a combined patient programmer/telemetry unit 501 as shown in FIG. 1B, or a mobile computing device 601 configured with patient programmer functionality as shown in FIG. 1C. Alternatively, the method 900 may be performed by the implantable drug delivery device 101, and the logic for determining whether a requested patient modification to the programmed drug delivery regimen is permitted may reside on the implantable device 101 itself.

In block 901 of method 900, a connection may be established with a mobile computing device, such as mobile computing device 301 shown in FIGS. 1A-1D. In block 903, at least one parameter for patient modification of a programmed drug delivery regimen is received. The at least one parameter may relate to the number of bolus doses of a drug that a patient may request in a predetermined time period, the volume of drug administered per bolus, a minimum wait time between administering bolus doses, time(s) of day in which bolus doses may be administered, an allowable modification to a basal rate of drug delivery that a patient may request etc. In block 907, the at least one parameter may be stored in a memory of the patient programmer.

In block 905, the at least one received parameter may be stored in memory, such as in internal memory 407 of a patient programmer unit 401. In optional block 907, a confirmation may be sent to the programming mobile computing device 301 that the programming of the parameters was successful. Alternatively, where the programming was not successful, a message may be sent to the mobile computing device 301 to indicate that the programming was unsuccessful. In block 909, the connection with the mobile computing device 301 may be ended.

Figure 6:
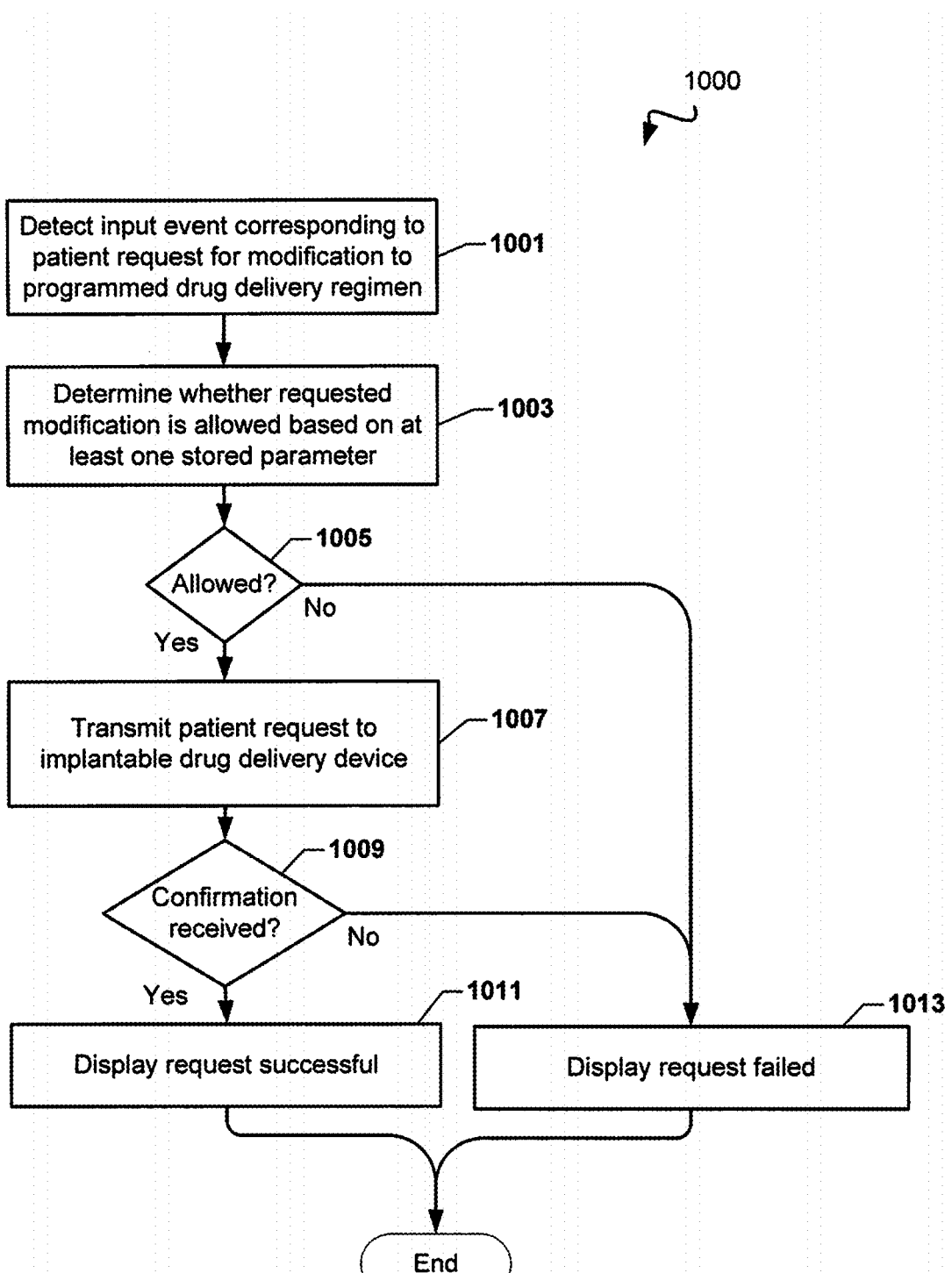
FIG. 6 is a process flow diagram illustrating an embodiment method of controlling operation of an implantable drug delivery device using a patient programmer.

FIG. 6 is a process flow diagram illustrating an embodiment method 1000 of patient modification of a programmed drug delivery regimen in an implantable drug delivery device. The method 1000 of FIG. 6 may be performed by a patient programmer, such as a patient programmer unit 401 as shown in FIGS. 1A and 1D, a combined patient programmer/telemetry unit 501 as shown in FIG. 1B, or a mobile computing device 601 configured with patient programmer functionality as shown in FIG. 1C. The method 1000 may be performed by a processor of a patient programmer that is coupled to a memory and configured with processor-executable instructions for performing the various steps of the method. The memory may contain stored parameters for allowable patient modifications to a drug delivery regimen, which may be programmed by a mobile computing device 301, as described above in connection with FIG. 4. Alternatively, all or a portion of the method 1000 may be performed by the implantable drug delivery device 101, such as where the logic for determining whether a requested patient modification to the programmed drug delivery regimen resides on the implantable device 101.

In block 1001 of method 1000, the patient programmer may detect an input event corresponding to a patient request for modification to a programmed drug delivery regimen. The input event may be, for example, a button push by a patient on the patient programmer. The input event may correspond to a request for an additional dose of a drug (i.e., a bolus dose) from the implantable drug delivery device 101.

In block 1003 of method 1000, a determination may be made as to whether the requested modification is allowable based on at least one stored parameter. The stored parameter(s) may relate to the number of bolus doses of a drug that a patient may request in a predetermined time period, the volume of drug administered per bolus, a minimum wait time between administering bolus doses, time(s) of day in which bolus doses may be administered, etc. The parameters may have been previously set by a physician or other medical professional, and stored in memory of the patient programmer. In determination block 1005, the processor of the patient programmer may determine whether the requested modification is allowed. In response to determining the requested modification is allowed (i.e., determination block 1005="Yes"), the processor of the patient programmer may transmit the patient request to the implantable drug delivery device 101 in block 1007. In determination block 1009, the processor of the patient programmer may determine whether a confirmation is received that the request has been successfully received and implemented by the implantable drug delivery device 101. In response to determining that the confirmation is received (i.e., determination block 1009="Yes"), the processor of the patient programmer may display that the patient request was successful in block 1011. In response to a determination that the requested modification is not allowed (i.e., determination block 1005="No"), or in response to a determination that no confirmation is received from the implantable device (i.e., determination block 1009="No"), the processor of the patient programmer may display that the patient request was unsuccessful in block 1013.

Various embodiments include a telemetry unit for an implantable drug delivery device that may be coupled to a mobile computing device (e.g., a smartphone, tablet, PDA, etc.) for programming of the implantable drug delivery device. In some embodiments, after programming, the mobile computing device may be removed from the telemetry unit, and a patient programmer may be coupled to the telemetry unit for enabling patient requested modifications to a programmed drug delivery regimen. In other embodiments, after programming the mobile computing device may be removed from the telemetry unit and a patient programmer may be coupled to a different telemetry unit for enabling patient requested modifications to the programmed drug delivery regimen. A first embodiment of a telemetry unit 1101 is illustrated in FIGS. 7A-G. FIG. 7A is an exploded view of the telemetry unit 1101 and a mobile computing device 301. FIG. 7B illustrates the telemetry unit 1101 coupled to mobile computing device 301. FIG. 7C is a cross-section view of the telemetry unit 1101 and FIG. 7D is a rear view of the telemetry unit 1101 coupled to the mobile computing device 301. As shown in the drawings, the telemetry unit 1101 in this embodiment includes a bottom housing 1103 that may include the transmitter/receiver element (e.g., telemetry coils) for wireless communication with the implantable drug delivery device, associated electronics and a power source (e.g., one or more batteries). A top cover 1105 may be secured to the bottom housing 1103, as shown in FIGS. 7B-D. A mobile computing device 301, such as a smartphone, may be mounted to the top cover 1105 as shown in FIGS. 7B and 7C. A three-way connector 1107 may be used to provide a data and/or power connection (e.g, a USB bridge) between the mobile computing device 301 and the telemetry unit 1101. The three-way connector 1107 may also include an external port 1109, such as a USB port. The top cover 1105 and bottom housing 1103 may be secured using a suitable fastening mechanism, such as internal crush pins. The top cover 1105 may be easily secured to the bottom housing 1103 and removed from the bottom housing 1103 by a user. Similarly, the top cover 1105 may be configured so that the mobile computing device 301 may easily snap into the top cover 1105 to secure the device 301 to the top cover 1105 and can be easily removed from the top cover 1105 after use. In embodiments, the top cover 1105 may be custom made to fit with a particular model of the mobile computing device 301. Various top covers 1105 may be made to fit with different models of mobile computing devices. The top cover 1105 may be designed such that the mobile computing device 301 is fully operable while the device 301 is mounted to the top cover 1105. The top cover 1105 may include one or more notches or cutouts 1111 at locations corresponding with the locations of buttons or switches (e.g., a power button) on the mobile computing device 301.

After the mobile computing device 301 has programmed the implantable drug delivery device and/or collected data from the implantable device, the top cover 1105 may be removed from the bottom housing 1103 and the mobile computing device 301 may be removed from the top cover 1105. In some embodiments, a patient programmer 1113 may then be secured to the bottom housing 1103, as shown in FIGS. 7E-G. FIG. 7E shows the patient programmer 1113 before it is secured to the bottom housing 1103. FIG. 7F is a front perspective view of the fully assembled telemetry unit 1101, and FIG. 7G is a rear view of the unit 1101. The patient programmer 1113 and bottom housing 1103 may be secured using a suitable fastening mechanism, such as internal crush pins. The patient programmer 1113 may be easily secured to the bottom housing 1103 and removed from the bottom housing 1103 as needed. The patient programmer 1113 includes a patient dosing button 1115 and LEDs 1117 that may provide indications of battery power, whether the telemetry coils are in wireless range of the implantable device, and whether a button push was successful. The button 1115 and indicators 1117 may be electrically connected to the electronics in the bottom housing 1103. The electronics for translating a button push into a wireless transmission to the implantable drug delivery device may be located in the patient programmer 1113 and/or the bottom housing 1103. Similarly, a processor and associated memory for determining whether a button push is allowable based on patient modification parameters stored in the memory may be located in the patient programmer 1113 and/or the bottom housing 1103.

Figure 8A:
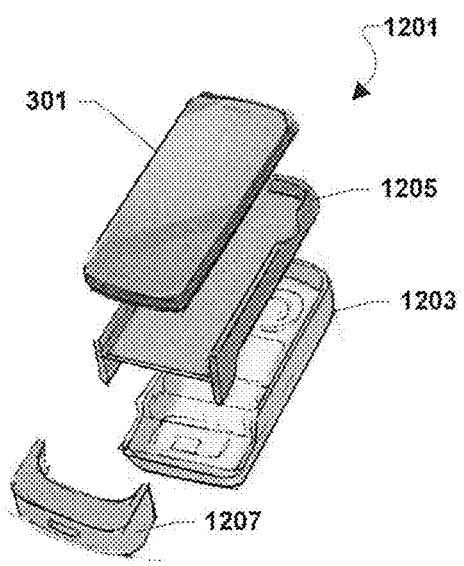
FIGS. 8A-8G illustrate a telemetry unit according to another embodiment.
Figure 8B:
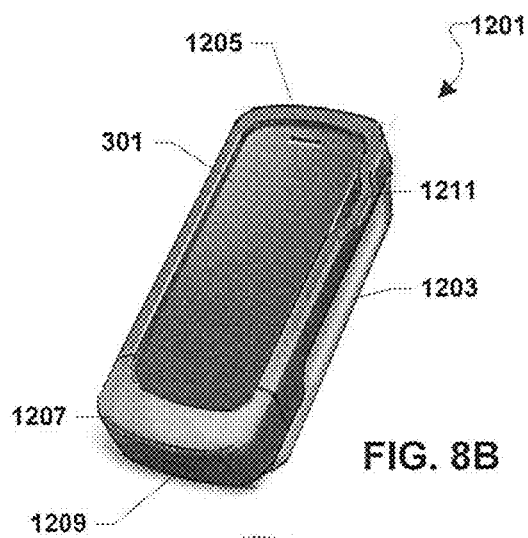
Figure 8C:
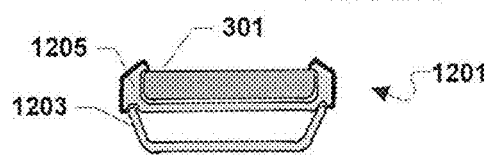
Figure 8D:
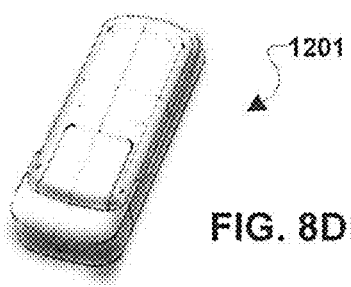

A second embodiment of a telemetry unit 1201 is illustrated in FIGS. 8A-G. FIG. 8A is an exploded view of the telemetry unit 1201 and a mobile computing device 301. FIG. 8B illustrates the telemetry unit 1201 coupled to mobile computing device 301. FIG. 8C is a cross-section view of the telemetry unit 1201 and FIG. 8D is a rear view of the telemetry unit 1201 coupled to the mobile computing device 301. Similar to the embodiment of FIGS. 7A-G, the telemetry unit 1201 includes a bottom housing 1203 that may include the transmitter/receiver element (e.g., telemetry coils) for wireless communication with the implantable drug delivery device, associated electronics and a power source (e.g., one or more batteries). A top cover 1205, 1207 may secure over the bottom housing 1203, as shown in FIGS. 8B-D. The top cover 1205, 1207 in this embodiment may be a two-piece component, including a first piece 1205 that receives the mobile computing device 103, and a bottom piece 1207 that slides over the bottom of the mobile computing device 103 and provides a three-way data/power connection between the mobile computing device 301, the bottom housing 1203 and an external port 1209, such as a USB port. The top cover 1105 and bottom housing 1103 may be secured using a suitable fastening mechanism, such as screws. In embodiments, the top cover portions 1205, 1207 may be custom made to fit with a particular model of the mobile computing device 301. Various top covers 1205, 1207 may be made to fit with different models of mobile computing devices. The top cover 1205 may include one or more notches or cutouts 1211 at locations corresponding with the locations of buttons or switches (e.g., a power button) on the mobile computing device 301.

Figure 8E:
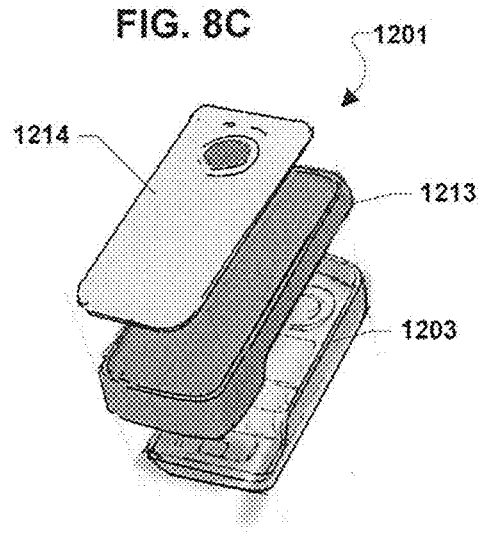
Figure 8F:
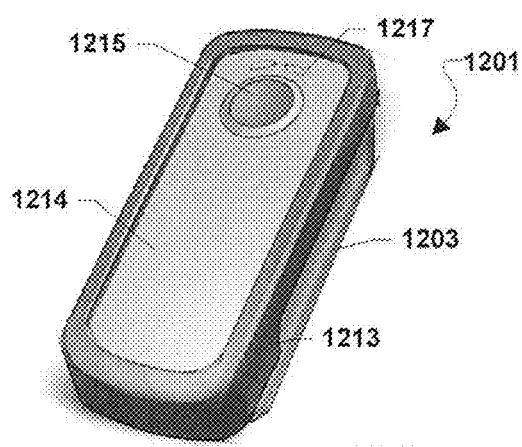
Figure 8G:
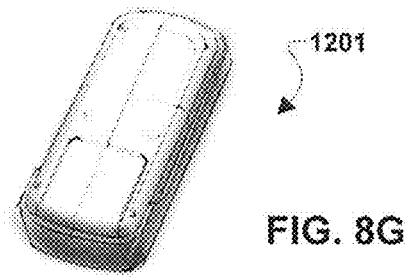

After the mobile computing device 301 has programmed the implantable drug delivery device and/or collected data from the implantable device, the top cover portions 1105, 1107 may be removed from the bottom housing 1203 and the mobile computing device 301 may be removed. In some embodiments, a patient programmer 1213, 1214 may then be secured to the bottom housing 1203, as shown in FIGS. 8E-G. FIG. 8E shows the patient programmer 1213, 1214 in an exploded view before it is secured to the bottom housing 1203. FIG. 8F is a front perspective view of the fully assembled telemetry unit 1201, and FIG. 8G is a rear view of the unit 1201. The patient programmer in this embodiment is a two-piece patient programmer that includes a top cover portion 1213, which may be secured to the bottom housing 1203 similar to the top cover 1205 shown in FIGS. 8A-D, and a membrane keypad 1214 with an embossed dosing button 1215 and LED indicators 1217. The button 1215 and indicators 1217 may be electrically connected to the electronics in the bottom housing 1203. The electronics for translating a button push into a wireless transmission to the implantable drug delivery device may be located in the patient programmer 1213, 1214 and/or the bottom housing 1203. Similarly, a processor and associated memory for determining whether a button push is allowable based on patient modification parameters stored in the memory may be located in the patient programmer 1213, 1214 and/or the bottom housing 1203.

A third embodiment of a telemetry unit 1301 is illustrated in FIGS. 9A-G. FIG. 9A is an exploded view of the telemetry unit 1301 and a mobile computing device 301. FIG. 9B illustrates the telemetry unit 1301 coupled to mobile computing device 301. FIG. 9C is a cross-section view of the telemetry unit 1301 and FIG. 9D is a rear view of the telemetry unit 1301 coupled to the mobile computing device 301. Similar to the embodiments of FIGS. 7A-G and 8A-G, the telemetry unit 1301 includes a bottom housing 1303 that may include the transmitter/receiver element (e.g., telemetry coils) for wireless communication with the implantable drug delivery device, associated electronics and a power source (e.g., one or more batteries). A top cover 1305 may secure over the bottom housing 1303 to sandwich a mobile computing device 301 between the top cover 1305 and bottom housing 1303, as shown in FIGS. 9A-D. The electronics for data connection and charging may be contained in the bottom housing 1303. The top cover 1305 may include a slot or opening for access to an external port 1309, such as a USB port. The top cover 1205 and bottom housing 1203 may be secured using a suitable fastening mechanism, such as screws. In embodiments, the top cover 1305 may be custom made to fit with a particular model of the mobile computing device 301. Various top covers 1305 may be made to fit with different models of mobile computing devices. The top cover 1305 may include one or more molded switches 1311 at locations corresponding with the locations of buttons or switches (e.g., a power button) on the mobile computing device 301.

After the mobile computing device 301 has programmed the implantable drug delivery device and/or collected data from the implantable device, the top cover 1305 may be removed from the bottom housing 1303 and the mobile computing device 301 may be removed. In some embodiments, a patient programmer 1313 may then be secured to the bottom housing 1303, as shown in FIGS. 9E-G. FIG. 9E shows the patient programmer 1313 before it is secured to the bottom housing 1303. FIG. 9F is a front perspective view of the fully assembled telemetry unit 1301, and FIG. 9G is a rear view of the unit 1301. The patient programmer 1313 and bottom housing 1303 may be secured using a suitable fastening mechanism, such as screws. The patient programmer 1313 may be easily secured to the bottom housing 1103 and removed from the bottom housing 1103 as needed. The patient programmer 1313 includes a patient dosing button 1315 and LEDs 1317 that may provide indications of battery power, whether the telemetry coils are in wireless range of the implantable device, and whether a button push was successful. The button 1315 and indicators 1317 may be electrically connected to the electronics in the bottom housing 1303. The electronics for translating a button push into a wireless transmission to the implantable drug delivery device may be located in the patient programmer 1313 and/or the bottom housing 1303. Similarly, a processor and associated memory for determining whether a button push is allowable based on patient modification parameters stored in the memory may be located in the patient programmer 1313 and/or the bottom housing 1303.

Figure 10A:
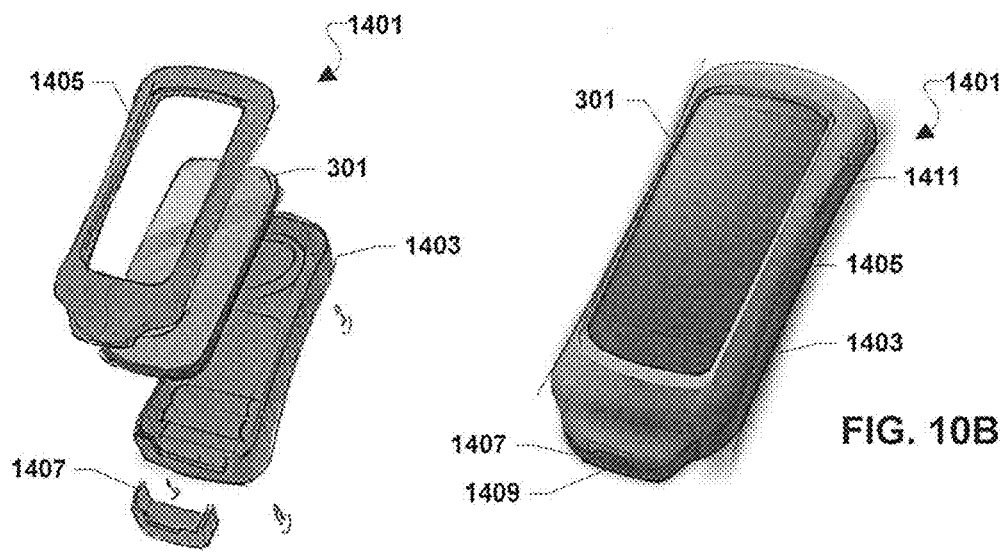
Figure 10C:
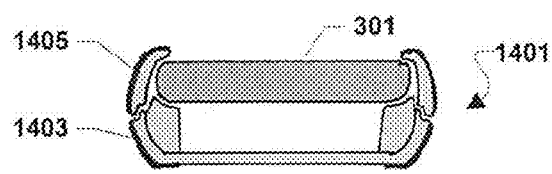
Figure 10D:
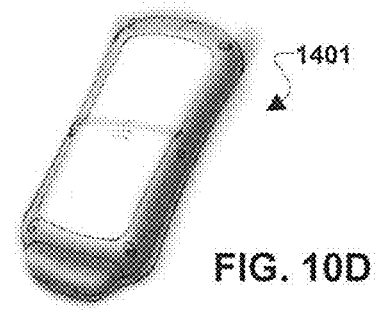

A fourth embodiment of a telemetry unit 1401 is illustrated in FIGS. 10A-G. FIG. 10A is an exploded view of the telemetry unit 1401 and a mobile computing device 301. FIG. 10B illustrates the telemetry unit 1401 coupled to mobile computing device 301. FIG. 10C is a cross-section view of the telemetry unit 1401 and FIG. 10D is a rear view of the telemetry unit 1401 coupled to the mobile computing device 301. Similar to the embodiments of FIGS. 7A-G, 8A-G and 9A-G, the telemetry unit 1401 includes a bottom housing 1403 that may include the transmitter/receiver element (e.g., telemetry coils) for wireless communication with the implantable drug delivery device, associated electronics and a power source (e.g., one or more batteries). A top cover 1405 may secure over the bottom housing 1403 to sandwich a mobile computing device 301 between the top cover 1405 and bottom housing 1403, as shown in FIGS. 10A-D. A separate connector component 1407 containing a three-way connector and external (e.g., USB) port may attach to the top cover 1405 and bottom housing 1403, as shown in FIGS. 10A-D. (The separate connector component 1407 may not be used with the patient programmer 1413 to reduce footprint). The top cover 1405 and bottom housing 1403 may be secured using a suitable fastening mechanism, such as screws. In embodiments, the top cover 1405 may be custom made to fit with a particular model of the mobile computing device 301. Various top covers 1405 may be made to fit with different models of mobile computing devices. The top cover 1405 may include one or more molded switches 1411 at locations corresponding with the locations of buttons or switches (e.g., a power button) on the mobile computing device 301.

Figure 10E:
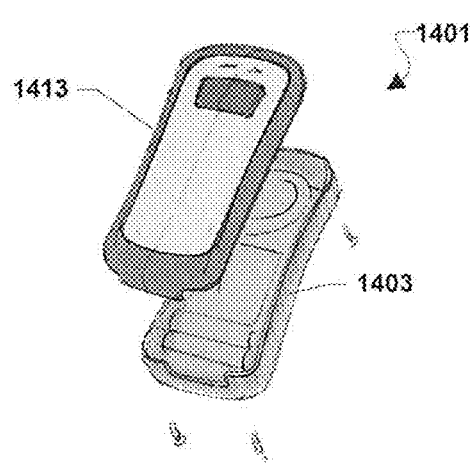
Figure 10F:
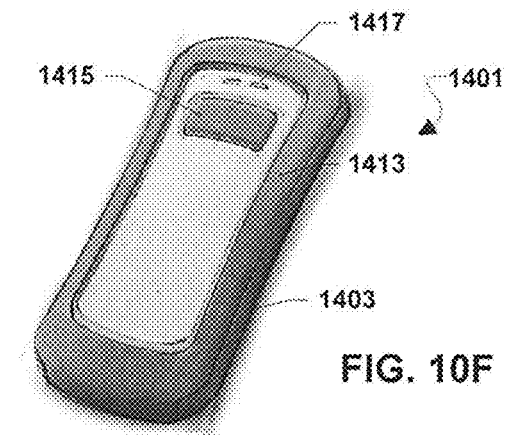
Figure 10G:
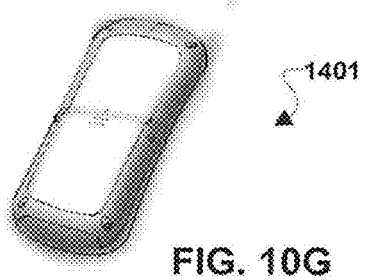

After the mobile computing device 301 has programmed the implantable drug delivery device and/or collected data from the implantable device, the top cover 1405 may be removed from the bottom housing 1403 and the mobile computing device 301 may be removed. In some embodiments, a patient programmer 1413 may then be secured to the bottom housing 1403, as shown in FIGS. 10E-G. FIG. 10E shows the patient programmer 1413 before it is secured to the bottom housing 1403. FIG. 10F is a front perspective view of the fully assembled telemetry unit 1401, and FIG. 10G is a rear view of the unit 1401. The patient programmer 1413 and bottom housing 1403 may be secured using a suitable fastening mechanism, such as screws. The patient programmer 1413 may be easily secured to the bottom housing 1403 and removed from the bottom housing 1403 as needed. The patient programmer 1413 includes a patient dosing button 1415 and LEDs 1417 that may provide indications of battery power, whether the telemetry coils are in wireless range of the implantable device, and whether a button push was successful. The button 1415 and indicators 1417 may be electrically connected to the electronics in the bottom housing 1403. The electronics for translating a button push into a wireless transmission to the implantable drug delivery device may be located in the patient programmer 1413 and/or the bottom housing 1403. Similarly, a processor and associated memory for determining whether a button push is allowable based on patient modification parameters stored in the memory may be located in the patient programmer 1413 and/or the bottom housing 1403.

Figure 11A:
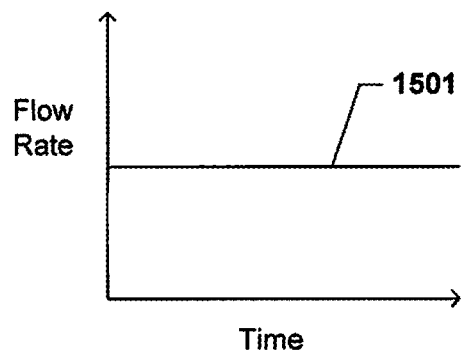
FIGS. 11A-11E are graphs illustrating alternative drug delivery regimens according to various embodiments.
Figure 11E:
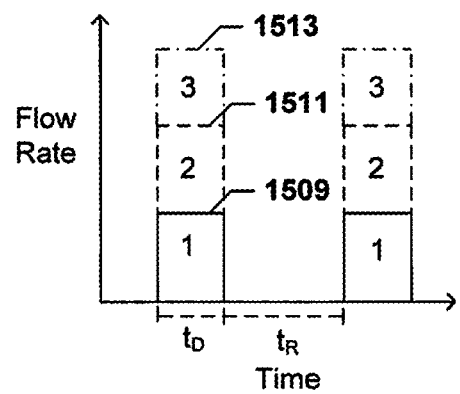
Figure 11B:
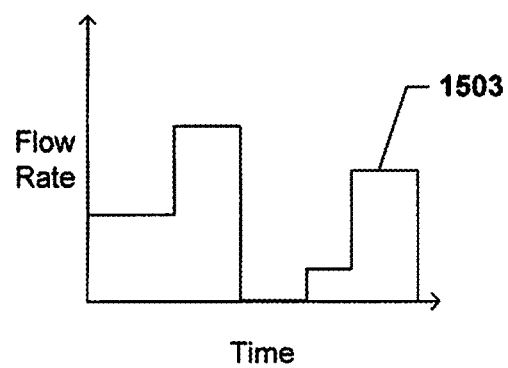
Figure 11C:
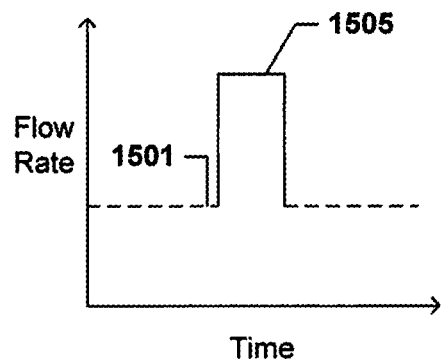
Figure 11D:
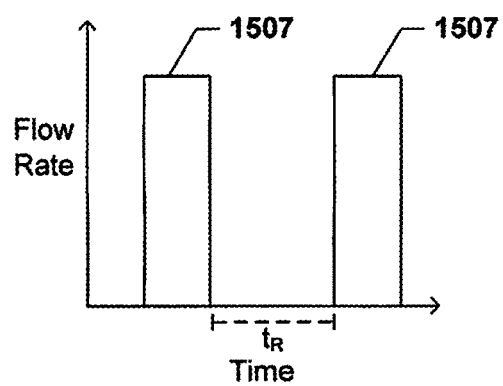

FIGS. 11A-11E are plots that illustrate various flow regimens that may programmed into a drug delivery device and used to control the delivery of a drug (the infusate) to a patient according to various embodiments. In FIGS. 11A-11D, volumetric flow rate of infusate is shown as a function of time. FIG. 11A illustrates a drug delivery regimen featuring a constant flow rate 1501 over time. FIG. 11B illustrates a drug delivery regimen featuring a flow rate 1503 that varies over time. FIG. 11C illustrates a drug delivery regimen featuring a a basal flow rate 1501 (which may be constant as shown in FIG. 11A or variable as shown in FIG. 11B) with periodic delivery of bolus doses 1515 of the drug, which may be delivered on a programmed basis and/or on an as-needed basis in response to a patient request. FIG. 11D illustrates a periodic drug delivery regimen in which the infusate may be delivered via a programmed series of delivery pulses 1507 (i.e., boluses), with no infusate delivered between the delivery pulses 1507. The patient may optionally have the ability to administer additional bolus doses on an as-needed basis.

A drug delivery regimen may include various combinations of one or more of the flow rate schemes illustrated in FIGS. 11A-11D. In some embodiments, a particular dosage of infusate may be delivered in the form of a plurality of pulses or boluses of the infusate that provide a total quantity of the dosage over a treatment period, as described in commonly-owned U.S. Pat. No. 9,180,282, which is incorporated by reference herein. The period between the boluses may be selected to provide a prophylactic treatment to avoid granuloma formation in the tissue proximate to the delivery site.

Instead of a pre-programmed scheduled drug delivery regimen, a drug delivery regimen may include delivery by user-selection of bolus doses only. This may be referred to as a user-selected bolus dose drug delivery regimen. In such a regimen, the patient may control the delivery of the bolus doses using a patient programmer unit, such as patient programmer units 401, 501 and 601 described above with reference to FIGS. 1A-1D. In this regimen, there may be no pre-programmed scheduled delivery of the drug to the patient, and the drug may be delivered to the patient exclusively via user-requested bolus doses.

In some embodiments, the physician may program the patient programmer unit and/or the drug delivery device to adhere to certain parameters or limits with respect to delivery of the infusate by bolus doses. For example, the programmed parameters may relate to the minimum wait time (i.e., refractory time) between the administration of bolus doses, the total number of bolus doses of a drug that the patient may administer in a predetermined time period (e.g., per day, per hour, per week, etc.), total quantity of drug that the patient may administer in a predetermined time period, time(s) of day in which bolus doses may be administered, etc.

For example, with reference to FIG. 11D, the physician may program a minimum refractory time ($t_R$) following the delivery of a patient-requested bolus dose 1507 before the patient can successfully request the delivery of another bolus dose. A request for another bolus dose within the minimum refractory time ($t_R$) will not be accepted (i.e., no infusate will be delivered by the drug delivery device in response to a patient request made on the patient programmer unit). Following the minimum refractory time ($t_R$), the patient may successfully request another bolus dose.

FIG. 11E graphically illustrates a further embodiment in which a patient programmer unit may be configured to enable a patient to select a particular size of bolus dose for delivery. For example, the patient programmer unit and/or the drug delivery device may be programmed to selectively deliver bolus doses of varying sizes (i.e., different volumes of the drug), such as the three sizes (1, 2, and 3) shown in FIG. 11E. The patient programmer unit may provide user-selectable options to enable a patient to select different size bolus doses (e.g., via separate hard keys/buttons on the patient programmer unit and/or via user-selectable menu options on a user interface display of the patient programmer unit). It will be understood that more or less than three different size bolus doses may be utilized. Further, although the different sizes of the bolus doses (i.e., sizes 1, 2 and 3) in FIG. 11E are illustrated as having different volumetric flow rates 1509, 1511 and 1513 over a given delivery time, $t_D$, the bolus dose size may also be adjusted by varying the delivery periods, $t_D$, or by varying the duty cycles of each bolus within a given delivery period, $t_D$.

In some embodiments, the physician may define the various size(s) of the bolus doses and/or restrict the size(s) of the bolus available to the patient when programming the device. The physician may further program limits on the number and frequency of bolus dose administration. In some embodiments, the ability for a patient to select particular bolus size (i.e., 1, 2 or 3) at a given time may be a function of one or more previously administered bolus doses. For example, following the administration of a relatively large dose (e.g., dose size 3), the minimum refractory time before the patient is allowed to administer another dose may be longer than the minimum refractory time following the administration of a relatively smaller dose (e.g., dose size 1 or 2). In addition, the minimum refractory time after a bolus dose is delivered may be variable based on the size of the subsequently requested bolus dose. For example, following the administration of a first bolus dose (e.g., a size 1 bolus dose), the minimum refractory time, $t_r$, before another size 1 bolus dose is allowed to be administered may be less than the minimum refractory time, $t_r$, before a larger (e.g., size 2 or 3) bolus dose may be administered.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary embodiments, the functions described may be implemented in hardware, software, firmware, or any combination thereof. If implemented in software, the functions may be stored as one or more instructions or code on a non-transitory computer-readable medium or non-transitory processor-readable medium. The steps of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A system, comprising:
   an implantable drug delivery device configured to deliver infusate according to a drug delivery regimen;
   a telemetry unit configured to communicate with the implantable drug delivery device;
   a mobile computing device configured to communicate with the telemetry unit and with a communication network; and
   a remote computing device configured to communicate with the mobile computing device via the communication network,
   wherein the mobile computing device is configured to communicate with the remote computing device via the communication network, and
   wherein the telemetry unit is configured to communicate with the implantable drug delivery device using a first communication interface and with the mobile computing device using a second communication interface different from the first communication interface, and
   wherein the remote computing device is configured to transmit information associated with the drug delivery regimen to the mobile computing device which is configured to transmit the information associated with the drug delivery regime to the telemetry unit which is configured to transmit the information associated with the drug delivery regime to the implantable drug delivery device.

2. The system of claim 1, wherein:
   the implantable drug delivery device is further configured to:
      store information associated with at least one of the drug delivery regimen, a status of the implantable drug delivery device, and physiological data of a patient associated with the implantable drug delivery device; and
      transmit the stored information to the telemetry unit;
   the telemetry unit is further configured to transmit the information received from the implantable drug delivery device to the mobile computing device; and
   the mobile computing device is further configured to transmit the information received from the telemetry unit to the remote computing device.

3. The system of claim 2, wherein the stored information includes at least one of a dosage history during the drug delivery regimen, an amount of drug delivered by the implantable drug delivery device during the drug delivery regimen, an amount of infusate remaining in a drug reservoir of the implantable drug delivery device, an indication of an amount of remaining power associated with the implantable drug delivery device, and information associated with malfunctions of the implantable drug delivery device.

4. The system of claim 1, wherein the telemetry unit is further configured to:
   receive a patient request to modify the drug delivery regimen;
   determine whether the requested modification to the drug delivery regimen is permissible; and
   communicate a command to the implantable drug delivery device in response to determining that the requested modification to the drug delivery regimen is permissible.

5. The system of claim 4, wherein the telemetry unit is further configured to transmit to the mobile computing device for relay to the remote computing device information related to requested modifications to the drug delivery regimen including one or more of information associated with at least one of a number of bolus doses requested within a predetermined time period of the drug delivery regimen, a volume of drug administered per each requested bolus dose, information associated with a time period between administered bolus doses, information associated with a time in which each bolus dose is administered, and information associated with a modification of a basal rate of delivery during the drug delivery regimen.

6. The system of claim 1, wherein the mobile computing device is further configured to:
   receive a patient request to modify the drug delivery regimen;
   determine whether the requested modification to the drug delivery regimen is permissible; and
   communicate a command to the implantable drug delivery device via the telemetry unit in response to determining that the requested modification to the drug delivery regimen is permissible.

7. The system of claim 6, wherein the mobile computing device is further configured to transmit to the remote computing device information related to requested modifications to the drug delivery regimen including one or more of information associated with at least one of a number of bolus doses requested within a predetermined time period of the drug delivery regimen, a volume of drug administered per each requested bolus dose, information associated with a time period between administered bolus doses, information associated with a time in which each bolus dose is administered, and information associated with a modification of a basal rate of delivery during the drug delivery regimen.

8. The system of claim 7, wherein the mobile computing device is further configured to receive a modification to the drug delivery regimen from the remote computer in response to transmitting the information related to requested modifications to the drug delivery regimen and communicate the modification to the drug delivery regimen received from the remote computer to the implantable drug delivery device via the telemetry unit.

9. The system of claim 1, further comprising a patient programmer configured to:

receive requests from a patient to modify the drug delivery regimen for the patient;

communicate instructions for modifying the drug delivery regime to the telemetry unit via a third communication link for relaying to the implantable drug delivery device; and transmit information to and received information from the mobile computing device via a fourth communication link different from the third communication link.

10. The system of claim 1, further comprising a server configured to:

receive information associated with the implantable drug delivery device from the mobile computing device over the communication network;

store the information associated with the implantable drug delivery device; and communicate with the remote computing device, wherein the remote computing device is configured to receive the information associated with the implantable drug delivery device by retrieving the information associated with the implantable drug delivery device stored at the server.

11. The system of claim 1, wherein the remote computing device is associated with a medical clinician.

12. The system of claim 1, wherein the remote computing device is further configured to diagnose, reprogram, or manage the implantable drug delivery device, the telemetry unit, or the mobile computing device from a location remote from a location of the implantable drug delivery device, the telemetry unit, or the mobile computing device.

13. A method of programming an implantable drug delivery device, comprising:

receiving from the implantable drug delivery device by a first telemetry unit via a first communication link information related to a patient in which the implantable drug delivery device is implanted, wherein the implantable drug delivery device is configured to administer an infusate according to a first drug delivery regimen;

relaying the information from the first telemetry unit to a mobile computing device via a second communication link different from the first communication link;

relaying the information from the mobile computing device to a remote computing device via a third communication link different from the first and second communication links;

receiving by the mobile computing device from the remote computing device via the third communication link a second drug delivery regimen to be implemented by the implantable drug delivery device;

relaying the second drug delivery regimen from the mobile computing device to the telemetry unit via the second communication link;

relaying the second drug delivery regimen from the telemetry unit to the implantable drug delivery device via the first communication link; and implementing the second drug delivery regimen by the implantable drug delivery device.

14. The method of claim 13, wherein the information related to the patient comprises one or more of a dosage history during the first drug delivery regimen, an amount of drug delivered by the implantable drug delivery device during the first drug delivery regimen, a number of times the patient requested a modification of the first drug delivery regimen, an amount of infusate remaining in a drug reservoir of the implantable drug delivery device, an indication of an amount of remaining power associated with the implantable drug delivery device, and information associated with malfunctions of the implantable drug delivery device.

15. The method of claim 13, further comprising:

transmitting from a second telemetry unit to the implantable drug delivery device the first drug delivery regimen, wherein the second telemetry unit is different from the first telemetry unit;

implementing the first drug delivery regimen by the implantable drug delivery device; and monitoring by a processor within the implantable drug delivery device operations of the implantable drug delivery device administering the infusate according to the first drug delivery regimen, wherein the information related to the patient comprises information obtained by the processor while monitoring operations of the implantable drug delivery device.

16. The method of claim 13, further comprising:

receiving an input from the patient at the mobile computing device, wherein the input requests a modification of the first drug delivery regimen;

determining whether the patient requested modification of the first drug delivery regimen is permissible;

transmitting from the mobile computing device to the first telemetry unit an instruction to implement the patient requested modification of the first drug delivery regimen in response to determining that the patient requested modification of the first drug delivery regimen is permissible;

transmitting from the first telemetry unit to the implantable drug delivery device the instruction to implement the patient requested modification of the first drug delivery regimen; and implementing the patient requested modification of the first drug delivery regimen by the implantable drug delivery device.

17. The method of claim 16, wherein:

the patient requested modification of the first drug delivery regimen comprises a request for an additional administration of the infusate; and implementing the patient requested modification of the first drug delivery regimen by the implantable drug delivery device comprises administering an additional bolus of infusate to the patient.

18. The method of claim 16, wherein determining whether the patient requested modification of the first drug delivery regimen is permissible comprises determining whether the patient requested modification is within a threshold of a parameter associated with the first drug delivery regimen.

19. The method of claim 13, further comprising:

displaying the information by the remote computing device in a format suitable for viewing by a physician; and receiving parameters defining the second drug delivery regimen as inputs from the physician; and transmitting the second drug delivery regimen from the remote computing device to the mobile computing device.

* * * * *